United States Patent
Weiner et al.

(10) Patent No.: US 9,034,313 B2
(45) Date of Patent: May 19, 2015

(54) NUCLEIC ACID MOLECULES ENCODING RANTES, AND COMPOSITIONS COMPRISING AND METHODS OF USING THE SAME

(75) Inventors: David B Weiner, Merion, PA (US); Jean D Boyer, Haddonfield, NJ (US); Michele Kutzler, Souderton, PA (US)

(73) Assignees: The Trustees of the University of Pennsylvania, Philadelphia, PA (US); Inovio Pharmaceuticals, Inc., Plymouth Meeting, PA (US)

( * ) Notice: Subject to any disclaimer, the term of this patent is extended or adjusted under 35 U.S.C. 154(b) by 78 days.

(21) Appl. No.: 13/577,387

(22) PCT Filed: Feb. 8, 2011

(86) PCT No.: PCT/US2011/024098
§ 371 (c)(1),
(2), (4) Date: Oct. 4, 2012

(87) PCT Pub. No.: WO2011/097640
PCT Pub. Date: Aug. 11, 2011

(65) Prior Publication Data
US 2013/0017224 A1   Jan. 17, 2013

Related U.S. Application Data

(60) Provisional application No. 61/302,324, filed on Feb. 8, 2010.

(51) Int. Cl.
| | |
|---|---|
| C07H 21/04 | (2006.01) |
| C12N 15/49 | (2006.01) |
| C12N 15/63 | (2006.01) |
| A61K 31/7088 | (2006.01) |
| C07K 14/52 | (2006.01) |
| A61K 39/21 | (2006.01) |
| C07K 14/47 | (2006.01) |
| C07K 14/435 | (2006.01) |
| A61K 48/00 | (2006.01) |
| A61K 39/00 | (2006.01) |

(52) U.S. Cl.
CPC .............. *C07K 14/523* (2013.01); *C07H 21/04* (2013.01); *A61K 31/7088* (2013.01); *A61K 48/00* (2013.01); *C07K 14/435* (2013.01); *C07K 14/47* (2013.01); *C12N 2740/16011* (2013.01); *C12N 2740/16034* (2013.01); *C12N 15/63* (2013.01); *A61K 39/21* (2013.01); *A61K 2039/53* (2013.01); *A61K 2039/545* (2013.01); *A61K 2039/55538* (2013.01); *A61K 2039/57* (2013.01); *C12N 2740/15034* (2013.01)

(58) Field of Classification Search
None
See application file for complete search history.

(56) References Cited

U.S. PATENT DOCUMENTS

| | | |
|---|---|---|
| 4,510,245 A | 4/1985 | Cousens et al. |
| 4,722,848 A | 2/1988 | Paoletti et al. |
| 4,790,987 A | 12/1988 | Compans et al. |
| 4,797,368 A | 1/1989 | Carter et al. |
| 4,920,209 A | 4/1990 | Davis et al. |
| 4,945,050 A | 7/1990 | Sanford et al. |
| 5,017,487 A | 5/1991 | Stunnenberg et al. |
| 5,036,006 A | 7/1991 | Sanford et al. |
| 5,077,044 A | 12/1991 | Stocker |
| 5,110,587 A | 5/1992 | Paoletti et al. |
| 5,112,749 A | 5/1992 | Brey, III et al. |
| 5,174,993 A | 12/1992 | Paoletti |
| 5,223,424 A | 6/1993 | Cochran et al. |
| 5,225,336 A | 7/1993 | Paoletti |
| 5,240,703 A | 8/1993 | Cochran |
| 5,242,829 A | 9/1993 | Panicali |
| 5,273,525 A | 12/1993 | Hofmann |
| 5,294,441 A | 3/1994 | Curtiss, III |
| 5,294,548 A | 3/1994 | Mclinden et al. |
| 5,310,668 A | 5/1994 | Ellis et al. |
| 5,387,744 A | 2/1995 | Curtiss, III et al. |
| 5,389,368 A | 2/1995 | Gurtiss, III |
| 5,424,065 A | 6/1995 | Curtiss, III et al. |
| 5,451,499 A | 9/1995 | Cochran |

(Continued)

FOREIGN PATENT DOCUMENTS

| | | |
|---|---|---|
| CN | 1168697 | 12/1997 |
| CN | 1832956 | 9/2006 |

(Continued)

OTHER PUBLICATIONS

Skolnick et al. From genes to protein structure and function: novel applications of computational approaches in the genomic era. Trends in Biotech 18(1): 34-39, 2000.*

Bork, A. Powers and pitfalls in sequence analysis: the 70% hurdle. Genome Res 10: 398-400, 2000.*

Doerks et al. Protein annotation: detective work for function prediction. Trends in Genetics 14(6): 248-250, 1998.*

(Continued)

*Primary Examiner* — Bridget E Bunner
(74) *Attorney, Agent, or Firm* — Riverside Law LLP

(57) ABSTRACT

Nucleic acid molecules comprising a nucleotide sequence encoding RANTES and fragments and variants thereof are disclosed. Additionally, nucleic acid molecules and compositions comprising the nucleotide sequence encoding RANTES and fragments and variants thereof in combination with nucleic acid sequences encoding immunogens are provided. Recombinant viral vectors comprising the nucleotide sequence encoding RANTES and fragments and variants thereof with or without a nucleic acid sequence encoding immunogens are also provided as are live attenuated pathogens comprising a nucleotide sequence encoding RANTES and fragments and variants thereof. Methods of modulating immune responses and of inducing an immune response against an immunogen are also disclosed.

30 Claims, 25 Drawing Sheets

(56) References Cited

U.S. PATENT DOCUMENTS

| | | | |
|---|---|---|---|
| 5,453,364 | A | 9/1995 | Paoletti |
| 5,462,734 | A | 10/1995 | Letchworth, III et al. |
| 5,470,734 | A | 11/1995 | Sondermeijer et al. |
| 5,474,935 | A | 12/1995 | Chatterjee et al. |
| 5,482,713 | A | 1/1996 | Paoletti |
| 5,580,859 | A | 12/1996 | Felgner et al. |
| 5,591,439 | A | 1/1997 | Plotkin et al. |
| 5,593,972 | A | 1/1997 | Weiner et al. |
| 5,643,579 | A | 7/1997 | Hung et al. |
| 5,650,309 | A | 7/1997 | Wong-Staal et al. |
| 5,676,594 | A | 10/1997 | Joosten |
| 5,698,202 | A | 12/1997 | Ertl et al. |
| 5,703,055 | A | 12/1997 | Felgner et al. |
| 5,739,118 | A | 4/1998 | Carrano et al. |
| 5,817,637 | A | 10/1998 | Weiner et al. |
| 5,830,876 | A | 11/1998 | Weiner et al. |
| 5,955,088 | A | 9/1999 | Ghiasi et al. |
| 5,962,428 | A | 10/1999 | Carrano et al. |
| 5,981,505 | A | 11/1999 | Weiner et al. |
| 6,034,298 | A | 3/2000 | Lam et al. |
| 6,042,836 | A | 3/2000 | Berman et al. |
| 6,110,161 | A | 8/2000 | Mathiesen et al. |
| 6,156,319 | A | 12/2000 | Cohen et al. |
| 6,159,711 | A | 12/2000 | Proudfoot et al. |
| 6,261,281 | B1 | 7/2001 | Mathiesen et al. |
| 6,589,529 | B1 | 7/2003 | Choi et al. |
| 6,697,669 | B2 | 2/2004 | Dev et al. |
| 6,939,862 | B2 | 9/2005 | Bureau et al. |
| 6,958,060 | B2 | 10/2005 | Mathiesen et al. |
| 7,238,522 | B2 | 7/2007 | Hebel et al. |
| 7,245,963 | B2 | 7/2007 | Draghia-Akli et al. |
| 7,328,064 | B2 | 2/2008 | Mathiesen et al. |
| 2005/0052630 | A1 | 3/2005 | Smith et al. |
| 2007/0041941 | A1 | 2/2007 | Weiner et al. |

FOREIGN PATENT DOCUMENTS

| | | |
|---|---|---|
| WO | 9416737 | 8/1994 |
| WO | 2008014521 | 1/2008 |
| WO | 2011161239 | 12/2011 |

OTHER PUBLICATIONS

Smith et al. The challenges of genome sequence annotation or "The devil is in the details". Nature Biotech 15: 1222-1223, 1997.*

Brenner, S.E. Errors in genome function. Trends in Genetics 15(4): 132-133, 1999.*

Bork et al. Go hunting in sequence databases but watch out for the traps. Trends in Genetics. 12(10): 425-427, 1996.*

Wells. J.A. Additivity of mutational effects in proteins. Biochemistry 29 (37): 8509-8517, 1990.*

Ngo et al. Computational complexity, protein structure prediction, and the Levinthal paradox. The Protein Folding Problem and Tertiary Structure Prediction, pp. 492-495, 1994.*

Tokuriki et al. Stablility effects of mutations and protein evolvability. Curr Opin Structural Biol 19: 596-604, 2009.*

Belisle et al. Long-term programming of antigen-specific immunity from gene expression signatures in the PBMC of rhesus macaques immunized with an SIV SNA vaccine. PLoS One: 6(6): e19681, 18 pages, 2011.*

Yin et al. SIV DNA vaccine co-delivered with plasmid expressing RANTES induce antigen specific cellular immune and lead to suppression of SIVmac251 replication. J Med Primatol 39(4): 296, #87; 2010; poster session Oct. 28-31, 2009.*

Andre, S. et al., "Increased immune response elicited by DNA vaccination with a synthetic gp120 sequence with optimized codon usage", J. Viral, 1998, 72(2):1497-1503.

Deml, L. et al., "Multiple effects of codon usage optimization on expression and immunogenicity of DNA candidate vaccines encoding the human immunodeficiency virius type 1 Gag protein", J. Viral, 2001, 75(22):1 0991-11001.

Laddy, D.J. et al., "Immunogenicity of novel consensus-based DNA vaccines against avian inftuenza", Vaccine, 2007, 25(16):2984-2989.

Frelin, L. et al., "Codon optimization and mRNA amplification effectively enhances the immunogenicity of the hepatitis C virus nonstructurai3/4A gene", Gene Therapy, 2004, 11(6):522-533.

Hirao, L.A. et al., "Intradermal subcutaneous immunization by electroporatlon improves plasmid vaccines delivery and potency in pigs and rhesus macaques", Vaccine, 2008, 26(3):440-448.

Luckay, A. et al., "Effect of plasmid DNA vaccine design and in vivo electroporation on the resulting vaccine-specific immune responses in rhesus macaques", J. Viral, 2007, 81(10):5257-5269.

Ahlen, G. et al., "In vivo electroporation enhances the immunogenicity of hepatitis C virus nonstructural 3/4A DNA by increased local DNA uptake, protein expression, inftammation, and infiltration of C[)3+ T cells", J. Immunol, 2007, 179(7):474-453.

Yan, J. et al., "Enhanced cellular immune responses elicited by an engineered HIV-1 subtype B consensus-based envelope DNA vaccine", Mol Ther, 2007, 152(2):411-421.

Rolland, M. et al., "Reconstruction and function of ancestral center-of-tree human in1munodeficiency virus type 1 proteins", J Viral, 2007, 81(16):8507-8514.

Hirao, L.A, "Enhancement of immune responses to DNA vaccines" Dissertations available from ProQuest. Paper AAI3414202. 2010 http://repository.upenn.edu/dissertations/AAI3414202.

Xin et al., "Immunization of RANTES expression plasmid with a DNA vaccine enhances HIV-1-specific immunity", Clin Immunol. Jul. 1999;92(1):90-6.

Kumar et al., "Immunogenicity testing of a novel engineered HIV-1 envelope gp140 DNA vaccine construct", DNA Cell Biol. Jul. 2006;25(7):383-92.

* cited by examiner

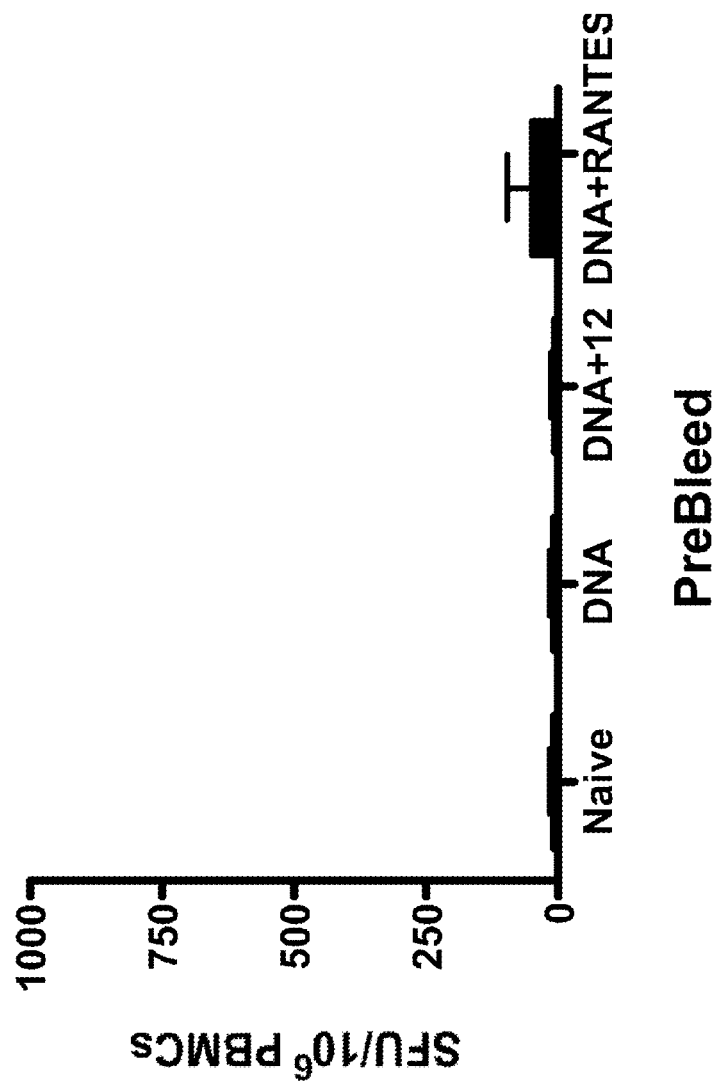

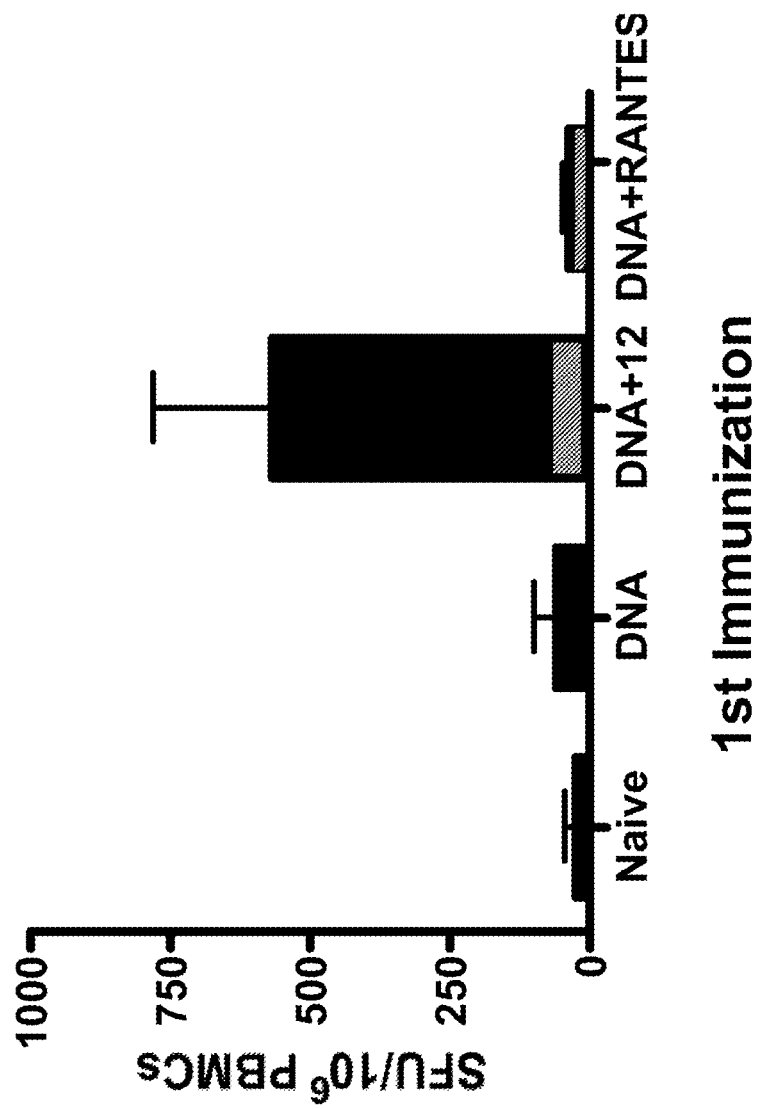

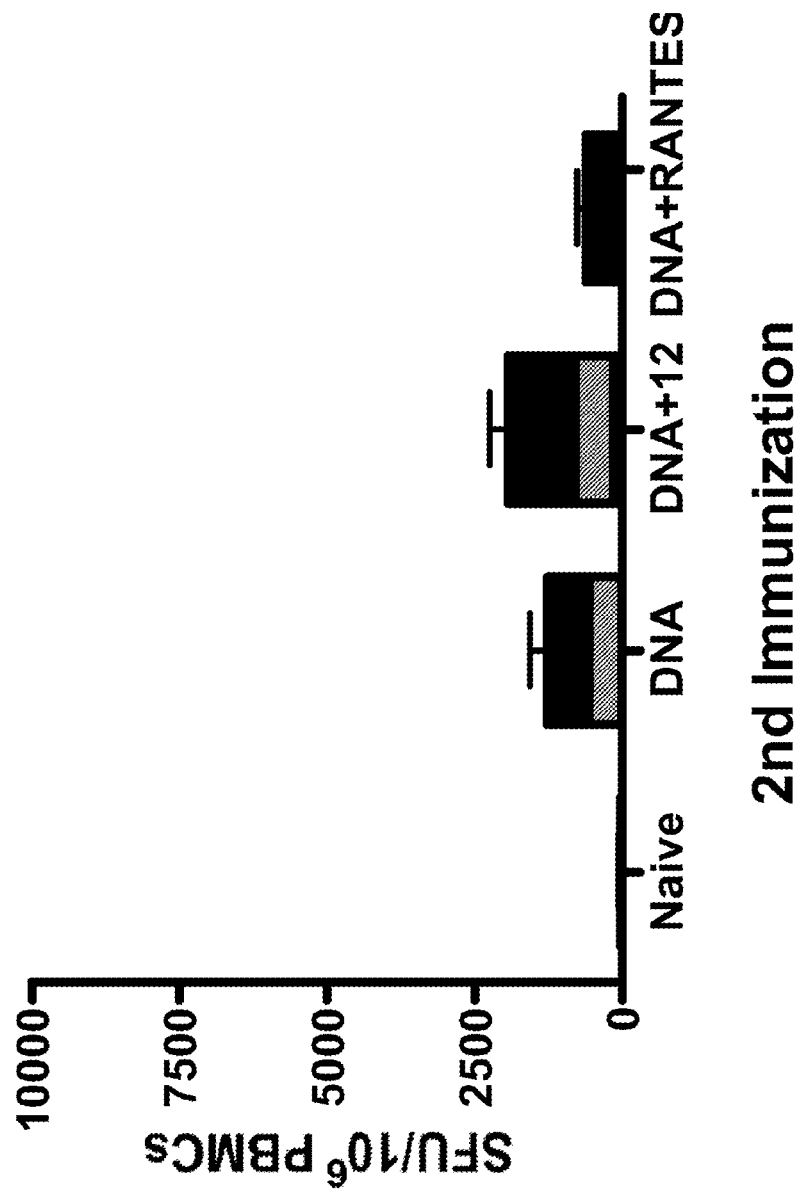

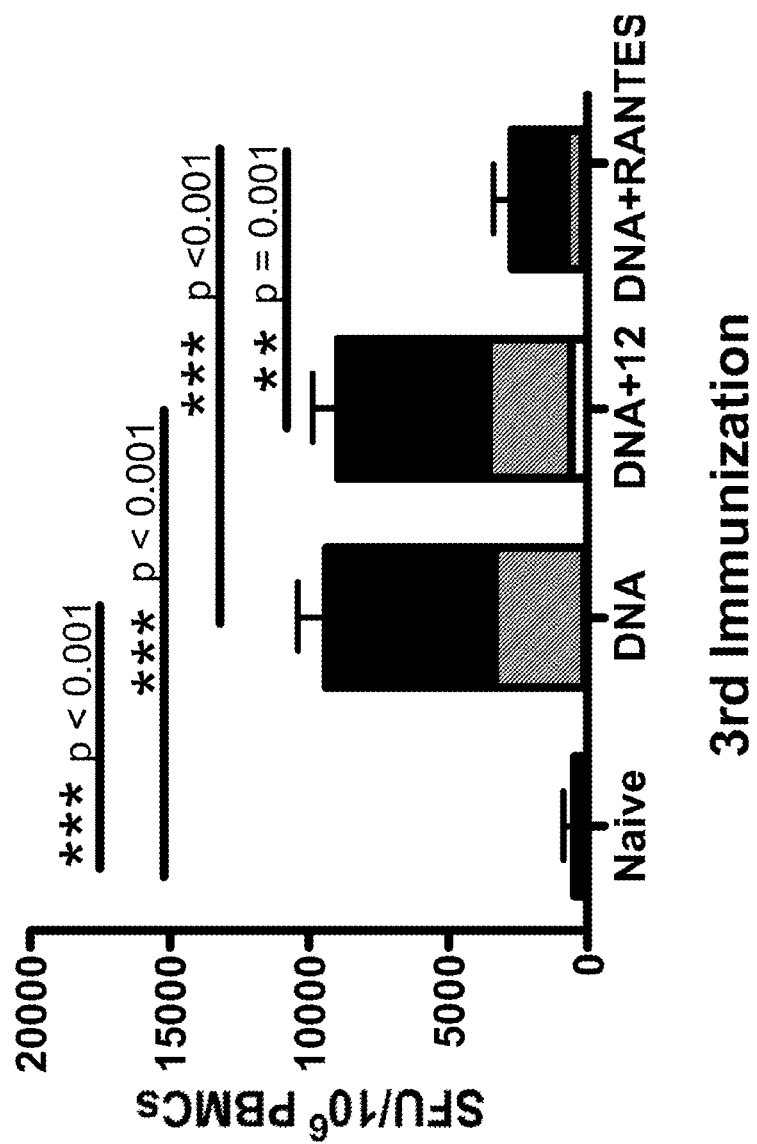

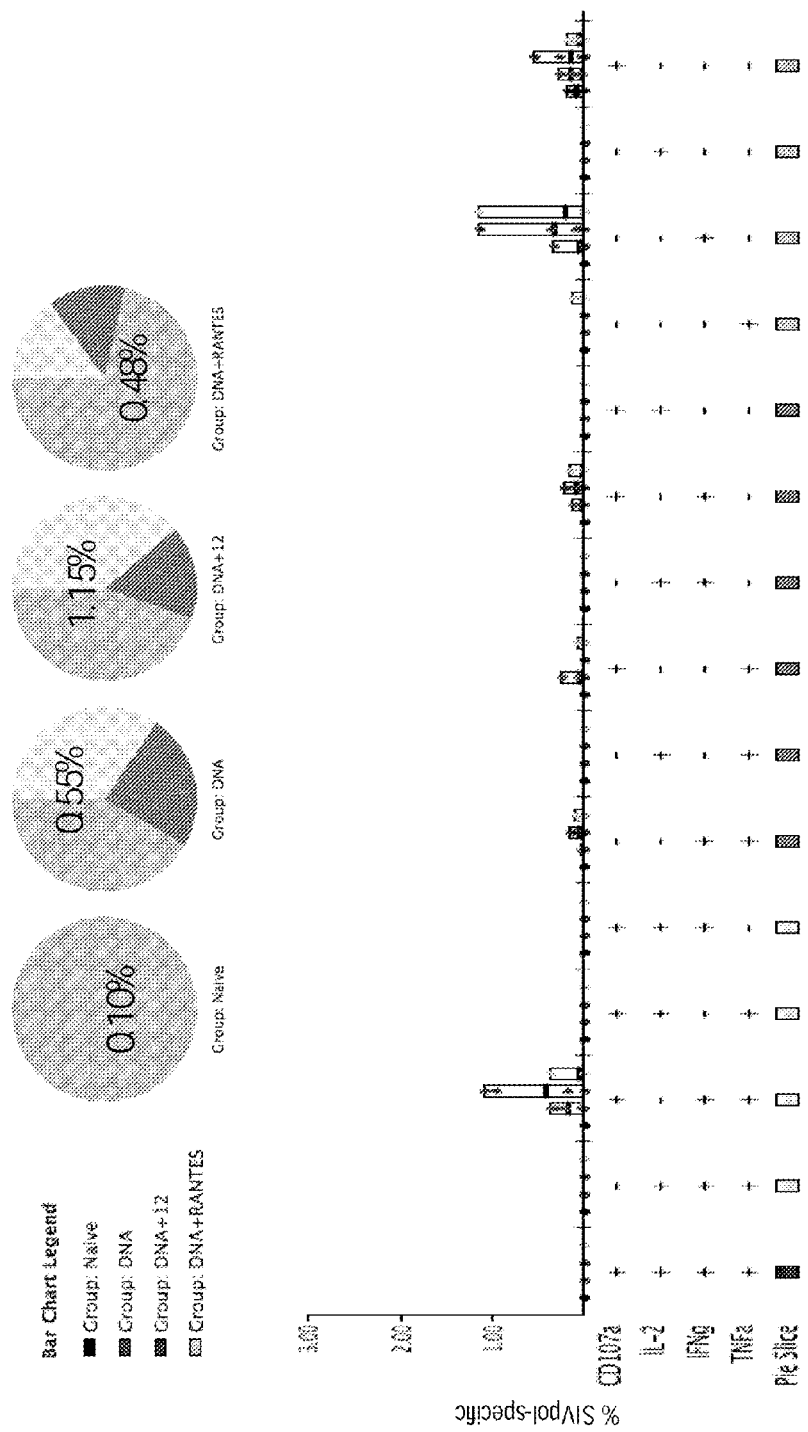

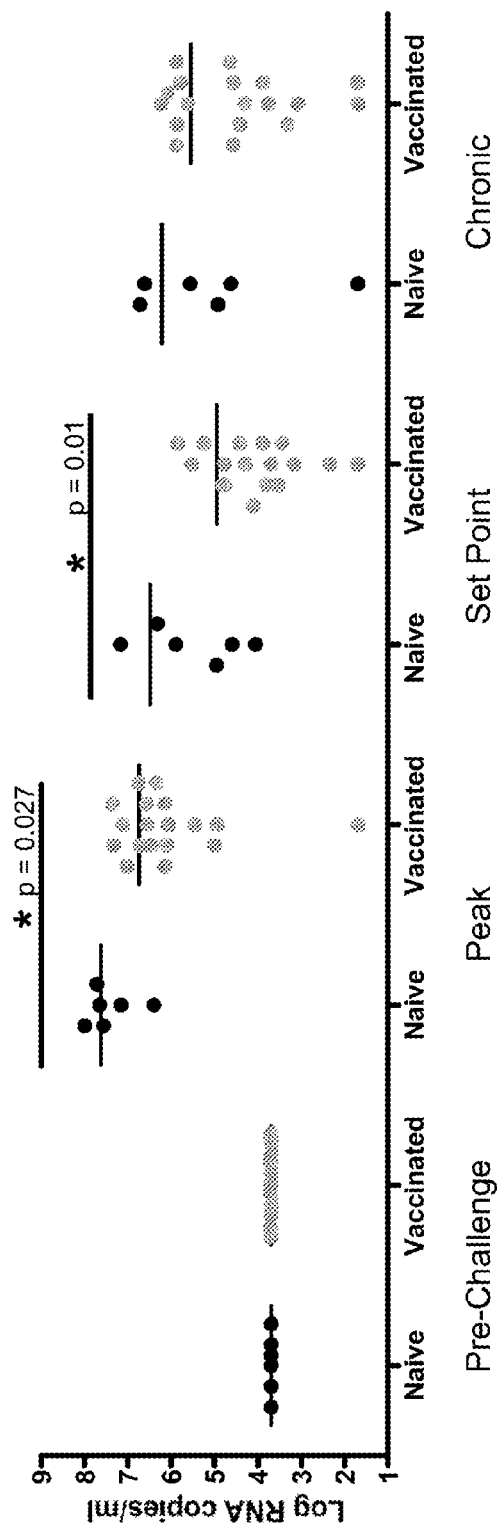

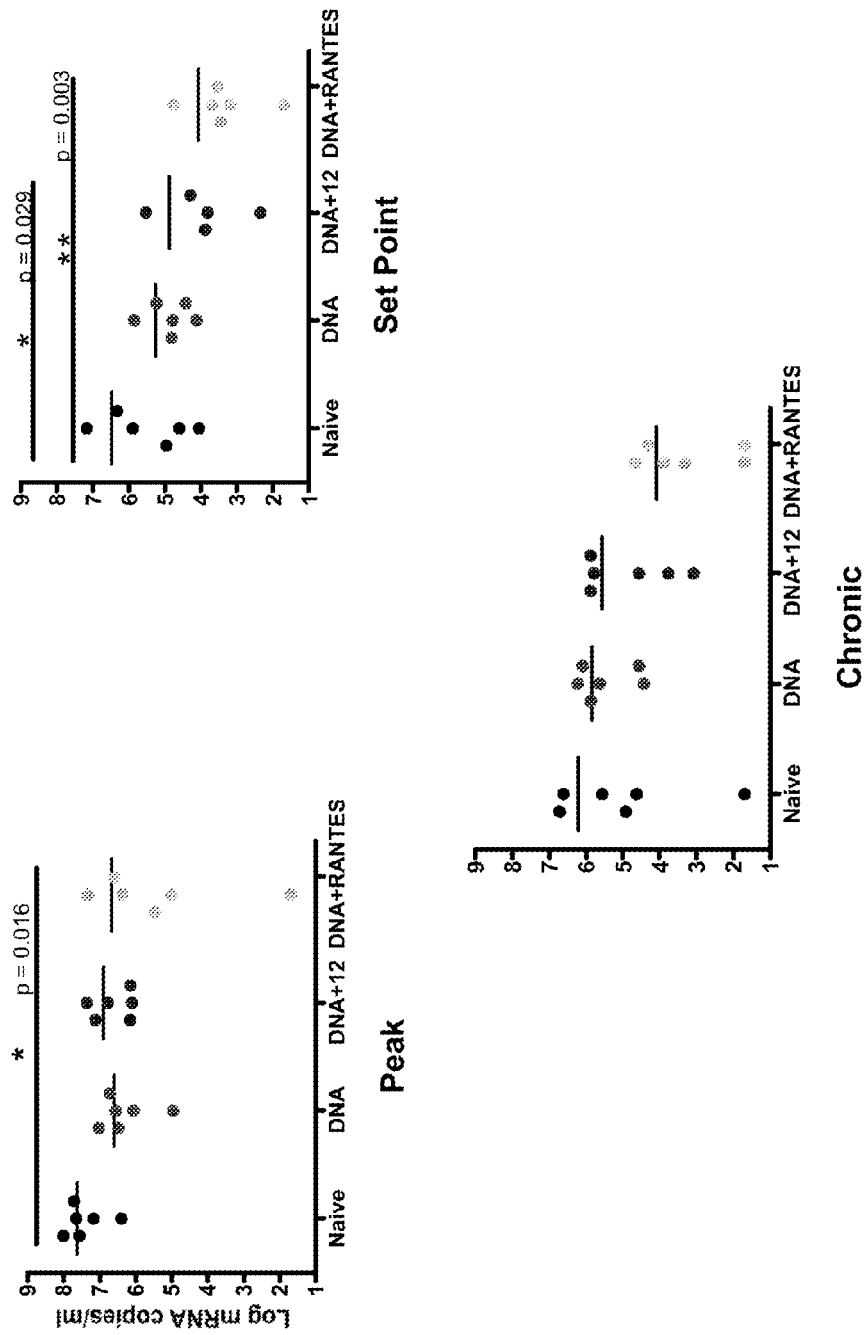

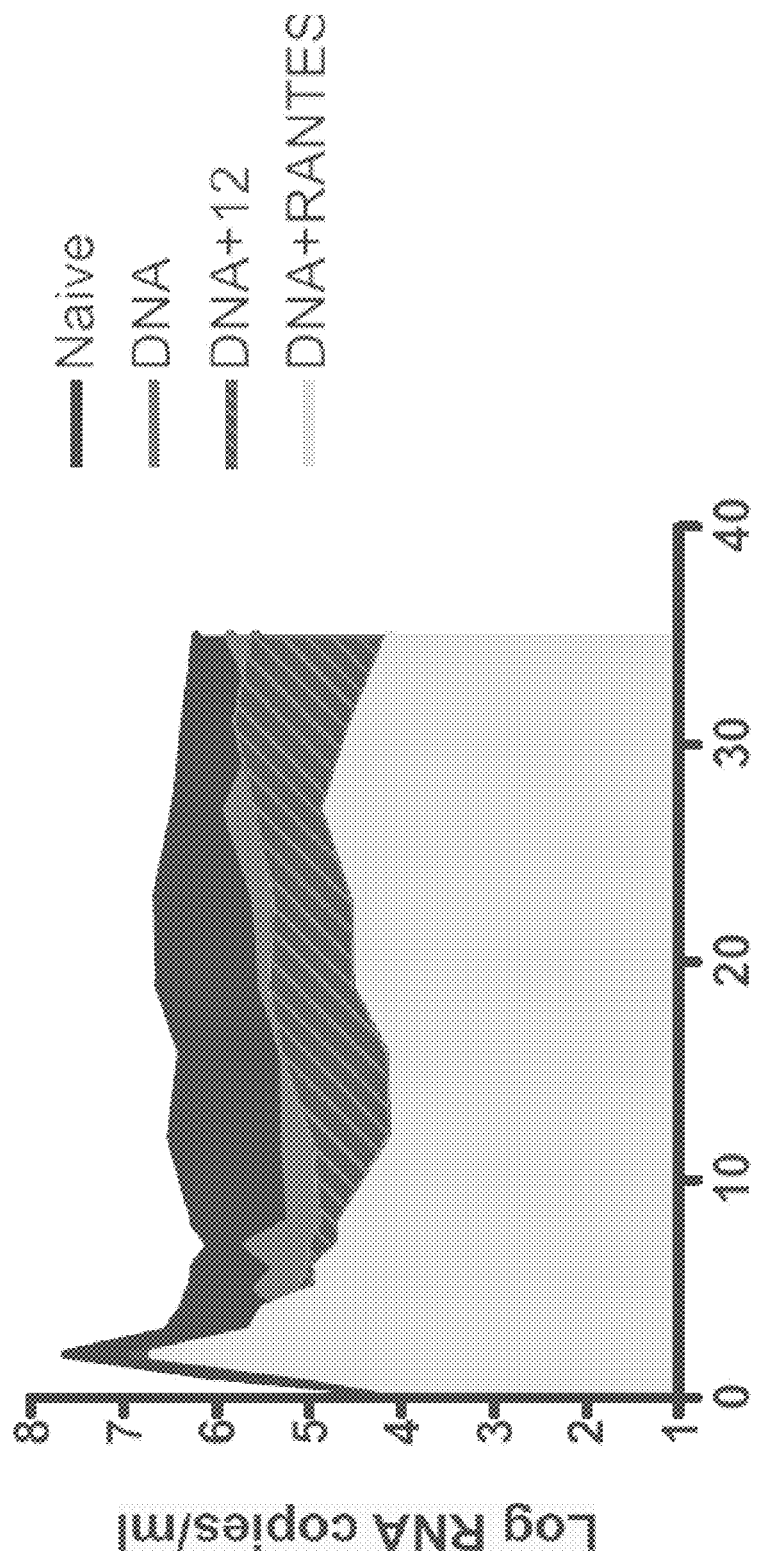

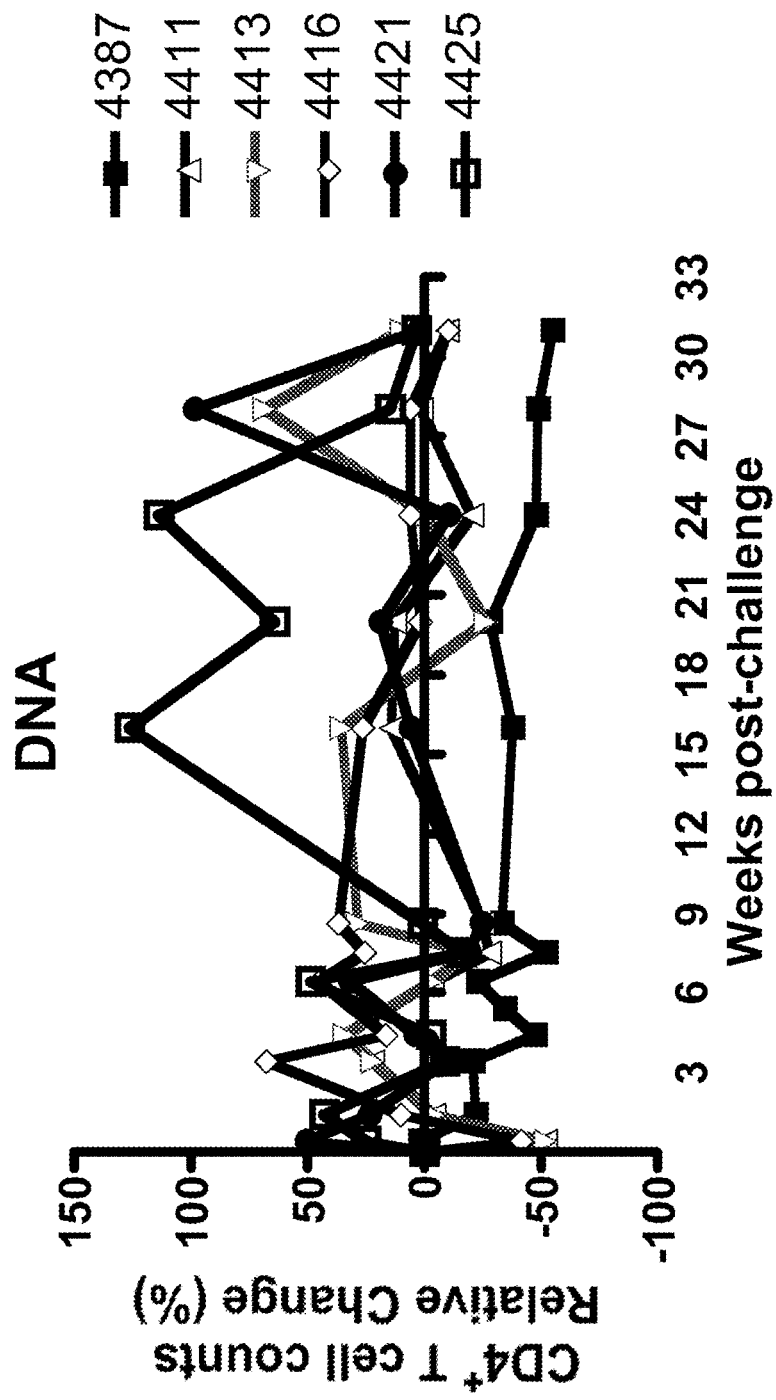

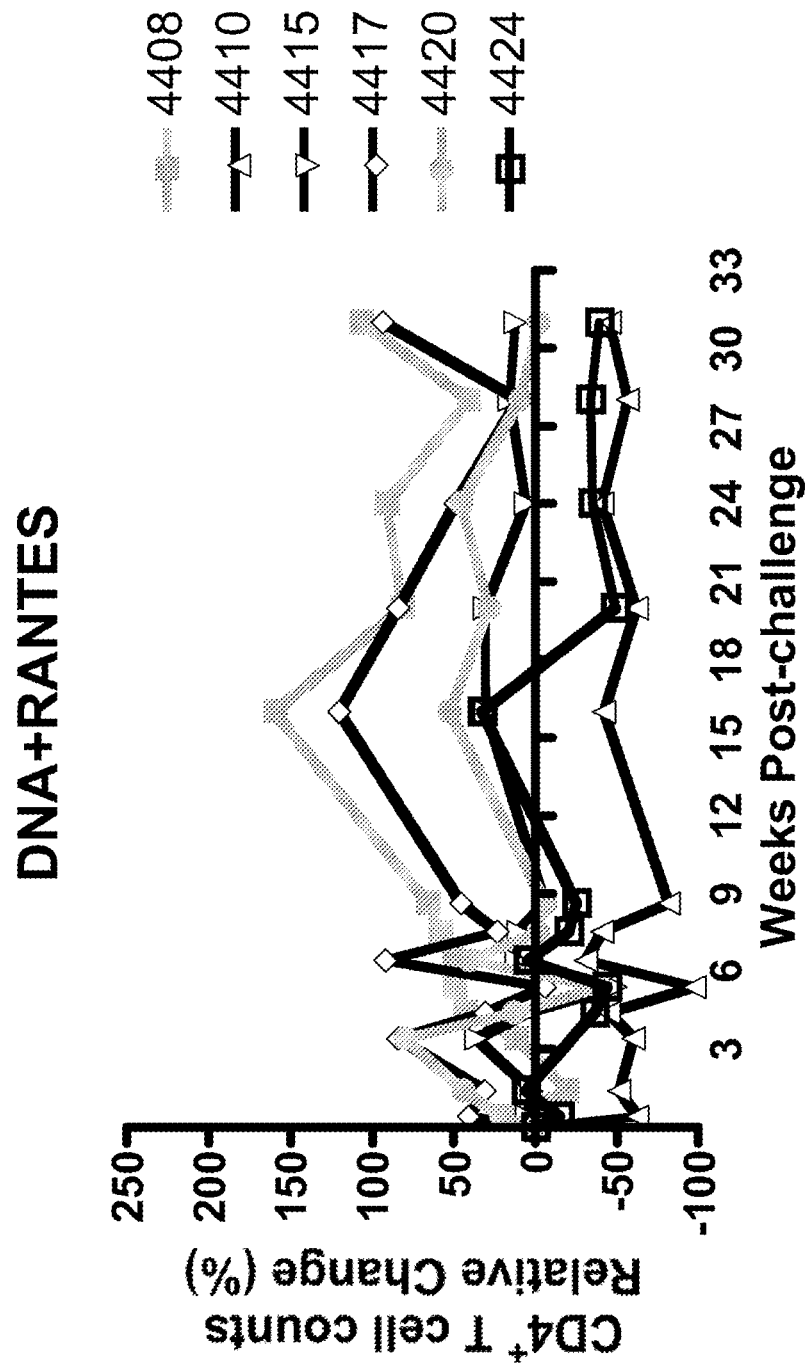

NUCLEIC ACID MOLECULES ENCODING RANTES, AND COMPOSITIONS COMPRISING AND METHODS OF USING THE SAME

CROSS-REFERENCE TO RELATED APPLICATIONS

This application claims priority to and is a United States National Stage filing under 35 USC §371 of International PCT Application Serial No. PCT/US2011/024098, filed Feb. 8, 2011, which claims priority to U.S. Provisional Application No. 61/302,324, filed Feb. 8, 2010, each of which is incorporated herein by reference in its entirety.

FIELD OF THE INVENTION

The present invention relates to nucleic acid molecules that encode RANTES. The invention relates to vaccines comprising the nucleotide sequence that encodes RANTES, and methods for prophylactically and/or therapeutically immunizing individuals against immunogens, and to immunotherapeutic compositions comprising the nucleotide sequence that encodes RANTES, and immunotherapy methods.

BACKGROUND OF THE INVENTION

This application claims priority to U.S. Provisional Application No. 61/302,324, which is incorporated herein by reference in its entirety.

RANTES, which is an abbreviation for Regulated upon Activation, Normal T-cell Expressed, and Secreted, is an 8 kDa protein classified as a chemotactic cytokine or chemokine, RANTES was identified as a gene expressed several days following T cell activation. A CC chemokine, RANTES, which has been found to be expressed many human diseases, is regulated in T lymphocytes by Kruppel like factor 13 (KLF13).

RANTES, which interacts with chemokine receptors CCR3, CCR5 and CCR1, is chemotactic for T cells, eosinophils, and basophils. It is involved in the recruitment of leukocytes into inflammatory sites. The combination of RANTES with cytokines IL-2 and IFN-γ, which are released by T cells, induces the proliferation and activation of certain natural-killer (NK) cells. Such cells are referred to as CHAK (CC-Chemokine-activated killer) cells.

U.S. application Ser. No. 09/622,452, which is incorporated herein by reference, discloses compositions and methods of using nucleic acid molecules that encode RANTES as immunotherapeutics and vaccines components. The expression of RANTES when used as an immunotherapeutic modifies certain aspects of the immune system in the individual in whom it is expressed. Similarly, expression of RANTES when used as part of a vaccine enhances certain aspects of the immune response against the vaccine immunogen.

Immunotherapy refers to modulating a person's immune responses to impart a desirable therapeutic effect. Immunotherapeutics refer to those compositions which, when administered to an individual, modulate the individual's immune system sufficient to ultimately decrease symptoms which are associated with undesirable immune responses or to ultimately alleviate symptoms by increasing desirable immune responses. In some cases, immunotherapy is part of a vaccination protocol in which the individual is administered a vaccine that exposes the individual to an immunogen against which the individual generates an immune response in such cases, the immunotherapeutic increases the immune response and/or selectively enhances a portion of the immune response (such as the cellular arm or the humoral arm) which is desirable to treat or prevent the particular condition, infection or disease.

Vaccine protocols can be improved by the delivery of agents that modulate a person's immune responses to induce an improved immune response. In some vaccination protocols in which the individual is administered a vaccine that exposes the individual to an immunogen against which the individual generates an immune response, an agent is provided that increases the immune response and/or selectively enhances a portion of the immune response (such as the cellular arm or the humoral arm) which is desirable to treat or prevent the particular condition, infection or disease.

Vaccines are useful to immunize individuals against target antigens such as allergens, pathogen antigens or antigens associated with cells involved in human diseases. Antigens associated with cells involved in human diseases include cancer-associated tumor antigens and antigens associated with cells involved in autoimmune diseases.

In designing such vaccines, it has been recognized that vaccines that produce the target antigen in cells of the vaccinated individual are effective in inducing the cellular arm of the immune system. Specifically, live attenuated vaccines, recombinant vaccines which use avirulent vectors and DNA vaccines each lead to the production of antigens in the cell of the vaccinated individual which results in induction of the cellular arm of the immune system. On the other hand, killed or inactivated vaccines, and sub-unit vaccines which comprise only proteins do not induce good cellular immune responses although they do induce an effective humoral response.

A cellular immune response is often necessary to provide protection against pathogen infection and to provide effective immune-mediated therapy for treatment of pathogen infection, cancer or autoimmune diseases. Accordingly, vaccines that produce the target antigen in cells of the vaccinated individual such as live attenuated vaccines, recombinant vaccines that use avirulent vectors and DNA vaccines are often preferred.

The direct administration of nucleic acid sequences to deliver proteins or vaccinate against animal and human diseases has been studied and much effort has been focused on effective and efficient means of nucleic acid delivery in order to yield necessary expression of the therapeutic/adjuvant protein and/or desired antigens.

DNA vaccines have many conceptual advantages over more traditional gene delivery and vaccination methods, such as live attenuated viruses and recombinant protein-based vaccines. DNA vaccines are safe, stable, easily produced, and well tolerated in humans with preclinical trials indicating little evidence of plasmid integration [Martin, T., et al., Plasmid DNA malaria vaccine: the potential for genomic integration after intramuscular injection. Hum Gene Ther, 1999. 10(5): p. 759-68; Nichols, W. W., et al., Potential DNA vaccine integration into host cell genome. Ann NY Acad Sci, 1995. 772: p. 30-9]. In addition, DNA vaccines are well suited for repeated administration due to the fact that efficacy of the vaccine is not influenced by pre-existing antibody titers to the vector [Chattergoon, M., J. Boyer, and D. B. Weiner, Genetic immunization: a new era in vaccines and immune therapeutics. FASEB J, 1997. 11(10): p. 753-63]. However, one major obstacle for the clinical adoption of DNA vaccines has been a decrease in the platform's immunogenicity when moving to larger animals [Liu, M. A. and J. B. Ulmer, Human clinical trials of plasmid DNA vaccines. Adv Genet, 2005. 55: p. 25-40]. Recent technological advances in the engineering of DNA vaccine immunogen, such has codon optimization, RNA optimization and the addition of immunoglobulin leader sequences have improved expression and immunogenicity of DNA vaccines [Andre, S., et al., Increased immune response elicited by DNA vaccination with a synthetic gp120 sequence with optimized codon usage. J Virol, 1998. 72(2): p. 1497-503; Deml, L., et al., Multiple effects of codon usage optimization on expression and immunogenicity of DNA candidate vaccines encoding the human immunodeficiency virus type 1 Gag protein. J Virol, 2001. 75(22): p. 10991-1001; Laddy, D. J., et al., Immunogenicity of novel consensus-based DNA vaccines against avian influenza. Vaccine, 2007. 25(16): p. 2984-9; Frelin, L., et al., Codon optimization and mRNA amplification effectively enhances the immunogenicity of the hepatitis C virus nonstructural 3/4A gene. Gene Ther, 2004. 11(6): p. 522-33], as well as, recently developed technology in plasmid delivery systems such as electroporation [Hirao, L. A., et al., Intradermal/subcutaneous immunization by electroporation improves plasmid vaccine delivery and potency in pigs and rhesus macaques. Vaccine, 2008. 26(3): p. 440-8; Luckay, A., et al., Effect of plasmid DNA vaccine design and in vivo electroporation on the resulting vaccine-specific immune responses in rhesus macaques. J Virol, 2007. 81(10): p. 5257-69; Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-53]. In addition, studies have suggested that the use of consensus immunogens can be able to increase the breadth of the cellular immune response as compared to native antigens alone [Yan, J., et al., Enhanced cellular immune responses elicited by an engineered HIV-1 subtype B consensus-based envelope DNA vaccine. Mol Ther, 2007. 15(2): p. 411-21; Rolland, M., et al., Reconstruction and function of ancestral center-of-tree human immunodeficiency virus type 1 proteins. J Viral, 2007. 81(16): p. 8507-14].

One method for delivering nucleic acid sequences such as plasmid DNA is the electroporation (EP) technique. The technique has been used in human clinical trials to deliver anti-cancer drugs, such as bleomycin, and in many preclinical studies on a large number of animal species.

While vaccines are often effective to immunize individuals prophylactically or therapeutically against pathogen infection or human diseases, there is a need for improved vaccines. There is a need for compositions and methods that produce an enhanced immune response. Likewise, while some immunotherapeutics are useful to modulate immune response in a patient there remains a need for improved immunotherapeutic compositions and methods.

SUMMARY OF THE INVENTION

The present invention relates to nucleic acid molecules comprising a nucleotide sequence selected from the group consisting of: SEQ ID NO:1, SEQ ID NO:3, SEQ ID NO:5, SEQ ID NO:7, a nucleic acid sequence that is 95% homologous to SEQ ID NO:1, a nucleic acid sequence that is 95% homologous to SEQ ID NO:3, a nucleic acid sequence that is 95% homologous to SEQ ID NO:5. a nucleic acid sequence that is 95% homologous to SEQ ID NO:7; a functional fragment of SEQ ID NO:1 comprising at least 60 nucleotides, a functional fragment of SEQ ID NO:3 comprising at least 60 nucleotides, a functional fragment of SEQ ID NO:5 comprising at least 60 nucleotides, a functional fragment of SEQ ID NO:7 comprising at least 60 nucleotides, a nucleic acid sequence that is 95% homologous to a functional fragment of SEQ ID NO:1 comprising at least 60 nucleotides, a nucleic acid sequence that is 95% homologous to a functional fragment of SEQ ID NO:3 comprising at least 60 nucleotides, a nucleic acid sequence that is 95% homologous to a functional fragment of SEQ ID NO:5 comprising at least 60 nucleotides and a nucleic acid sequence that is 95% homologous to a functional fragment of SEQ ID NO:7 comprising at least 60 nucleotides.

The present invention also relates to compositions comprising a plurality of one or more nucleic acid molecules comprising one or more nucleic acid sequences selected from the group consisting of: 1) a selected from the group consisting of: SEQ ID NO:1, SEQ ID NO:3, SEQ ID NO:5, SEQ ID NO:7, a nucleic acid sequence that is 95% homologous to SEQ ID NO:1, a nucleic acid sequence that is 95% homologous to SEQ ID NO:3, a nucleic acid sequence that is 95% homologous to SEQ ID NO:5. a nucleic acid sequence that is 95% homologous to SEQ ID NO:7; a functional fragment of SEQ ID NO:1 comprising at least 60 nucleotides, a functional fragment of SEQ ID NO:3 comprising at least 60 nucleotides, a functional fragment of SEQ ID NO:5 comprising at least 60 nucleotides, a functional fragment of SEQ ID NO:7 comprising at least 60 nucleotides, a nucleic acid sequence that is 95% homologous to a functional fragment of SEQ ID NO:1 comprising at least 60 nucleotides, a nucleic acid sequence that is 95% homologous to a functional fragment of SEQ ID NO:3 comprising at least 60 nucleotides, a nucleic acid sequence that is 95% homologous to a functional fragment of SEQ ID NO:5 comprising at least 60 nucleotides and a nucleic acid sequence that is 95% homologous to a functional fragment of SEQ ID NO:7 comprising at least 60 nucleotides; and b) one or more additional nucleic acid sequences that encode one or more immunogens.

The present invention additionally relates to methods of modulating an immune response comprising the step of administering to an individual a nucleic acid molecules comprising a nucleotide sequence selected from the group consisting of: SEQ ID NO:1, SEQ ID NO:3, SEQ ID NO:5, SEQ ID NO:7, a nucleic acid sequence that is 95% homologous to SEQ ID NO:1, a nucleic acid sequence that is 95% homologous to SEQ ID NO:3, a nucleic acid sequence that is 95% homologous to SEQ ID NO:5. a nucleic acid sequence that is 95% homologous to SEQ ID NO:7; a functional fragment of SEQ ID NO:1 comprising at least 60 nucleotides, a functional fragment of SEQ ID NO:3 comprising at least 60 nucleotides, a functional fragment of SEQ ID NO:5 comprising at least 60 nucleotides, a functional fragment of SEQ ID NO:7 comprising at least 60 nucleotides, a nucleic acid sequence that is 95% homologous to a functional fragment of SEQ ID NO:1 comprising at least 60 nucleotides, a nucleic acid sequence that is 95% homologous to a functional fragment of SEQ ID NO:3 comprising at least 60 nucleotides, a nucleic acid sequence that is 95% homologous to a functional fragment of SEQ ID NO:5 comprising at least 60 nucleotides and a nucleic acid sequence that is 95% homologous to a functional fragment of SEQ ID NO:7 comprising at least 60 nucleotides; or compositions comprising a plurality of one or more nucleic acid molecules comprising one or more nucleic acid sequences selected from the group consisting of 1) a selected from the group consisting of SEQ ID NO:1, SEQ ID NO:3, SEQ ID NO:5, SEQ ID NO:7, a nucleic acid sequence that is 95% homologous to SEQ ID NO:1, a nucleic acid sequence that is 95% homologous to SEQ ID NO:3, a nucleic acid sequence that is 95% homologous to SEQ ID NO:5. a nucleic acid sequence that is 95% homologous to SEQ ID NO:7; a functional fragment of SEQ ID NO:1 comprising at least 60 nucleotides, a functional fragment of SEQ ID NO:3 comprising at least 60 nucleotides, a functional fragment of SEQ ID NO:5 comprising at least 60 nucleotides, a functional fragment of SEQ ID NO:7 comprising at least 60 nucleotides, a nucleic acid sequence that is 95% homologous to a functional fragment of SEQ ID NO:1 comprising at least 60 nucleotides, a nucleic acid sequence that is 95% homologous to a functional fragment of SEQ ID NO:3 comprising at least 60 nucleotides, a nucleic acid sequence that is 95% homologous to a functional fragment of SEQ ID NO:5 comprising at least 60 nucleotides and a nucleic acid sequence that is 95% homologous to a functional fragment of SEQ ID NO:7 comprising at least 60 nucleotides; and b) one or more additional nucleic acid sequences that encode one or more immunogens.

The present invention further relates to recombinant viral vectors comprising a nucleotide sequence selected from the group consisting of: SEQ ID NO:1, SEQ ID NO:3, SEQ ID NO:5, SEQ ID NO:7, a nucleic acid sequence that is 95% homologous to SEQ ID NO:1, a nucleic acid sequence that is 95% homologous to SEQ ID NO:3, a nucleic acid sequence that is 95% homologous to SEQ ID NO:5. a nucleic acid sequence that is 95% homologous to SEQ ID NO:7; a functional fragment of SEQ ID NO:1 comprising at least 60 nucleotides, a functional fragment of SEQ ID NO:3 comprising at least 60 nucleotides, a functional fragment of SEQ ID NO:5 comprising at least 60 nucleotides, a functional fragment of SEQ ID NO:7 comprising at least 60 nucleotides, a nucleic acid sequence that is 95% homologous to a functional fragment of SEQ ID NO:1 comprising at least 60 nucleotides, a nucleic acid sequence that is 95% homologous to a functional fragment of SEQ ID NO:3 comprising at least 60 nucleotides, a nucleic acid sequence that is 95% homologous to a functional fragment of SEQ ID NO:5 comprising at least 60 nucleotides and a nucleic acid sequence that is 95% homologous to a functional fragment of SEQ ID NO:7 comprising at least 60 nucleotides.

The present invention also relates to methods of modulating an immune response in an individual comprising administering to said individual a recombinant viral vector comprising a nucleotide sequence selected from the group consisting of: SEQ ID NO:1, SEQ ID NO:3, SEQ ID NO:5, SEQ ID NO:7, a nucleic acid sequence that is 95% homologous to SEQ ID NO:1, a nucleic acid sequence that is 95% homologous to SEQ ID NO:3, a nucleic acid sequence that is 95% homologous to SEQ ID NO:5. a nucleic acid sequence that is 95% homologous to SEQ ID NO:7; a functional fragment of SEQ ID NO:1 comprising at least 60 nucleotides, a functional fragment of SEQ ID NO:3 comprising at least 60 nucleotides, a functional fragment of SEQ ID NO:5 comprising at least 60 nucleotides, a functional fragment of SEQ ID NO:7 comprising at least 60 nucleotides, a nucleic acid sequence that is 95% homologous to a functional fragment of SEQ ID NO:1 comprising at least 60 nucleotides, a nucleic acid sequence that is 95% homologous to a functional fragment of SEQ ID NO:3 comprising at least 60 nucleotides, a nucleic acid sequence that is 95% homologous to a functional fragment of SEQ ID NO:5 comprising at least 60 nucleotides and a nucleic acid sequence that is 95% homologous to a functional fragment of SEQ ID NO:7 comprising at least 60 nucleotides.

The present invention additionally relates to live attenuated pathogens comprising a nucleotide sequence selected from the group consisting of SEQ ID NO:1, SEQ ID NO:3, SEQ ID NO:5, SEQ ID NO:7, a nucleic acid sequence that is 95% homologous to SEQ ID NO:1, a nucleic acid sequence that is 95% homologous to SEQ ID NO:3, a nucleic acid sequence that is 95% homologous to SEQ ID NO:5. a nucleic acid sequence that is 95% homologous to SEQ ID NO:7; a functional fragment of SEQ ID NO:1 comprising at least 60 nucleotides, a functional fragment of SEQ ID NO:3 comprising at least 60 nucleotides, a functional fragment of SEQ ID NO:5 comprising at least 60 nucleotides, a functional fragment of SEQ ID NO:7 comprising at least 60 nucleotides, a nucleic acid sequence that is 95% homologous to a functional fragment of SEQ ID NO:1 comprising at least 60 nucleotides, a nucleic acid sequence that is 95% homologous to a functional fragment of SEQ ID NO:3 comprising at least 60 nucleotides, a nucleic acid sequence that is 95% homologous to a functional fragment of SEQ ID NO:5 comprising at least 60 nucleotides and a nucleic acid sequence that is 95% homologous to a functional fragment of SEQ ID NO:7 comprising at least 60 nucleotides.

The present invention also relates to methods of immunizing an individual against a pathogen comprising administering to said individual the live attenuated pathogen comprising a nucleotide sequence selected from the group consisting of: SEQ ID NO:1, SEQ ID NO:3, SEQ ID NO:5, SEQ ID NO:7, a nucleic acid sequence that is 95% homologous to SEQ ID NO:1, a nucleic acid sequence that is 95% homologous to SEQ ID NO:3, a nucleic acid sequence that is 95% homologous to SEQ ID NO:5. a nucleic acid sequence that is 95% homologous to SEQ ID NO:7; a functional fragment of SEQ ID NO:1 comprising at least 60 nucleotides, a functional fragment of SEQ ID NO:3 comprising at least 60 nucleotides, a functional fragment of SEQ ID NO:5 comprising at least 60 nucleotides, a functional fragment of SEQ ID NO:7 comprising at least 60 nucleotides, a nucleic acid sequence that is 95% homologous to a functional fragment of SEQ ID NO:1 comprising at least 60 nucleotides, a nucleic acid sequence that is 95% homologous to a functional fragment of SEQ ID NO:3 comprising at least 60 nucleotides, a nucleic acid sequence that is 95% homologous to a functional fragment of SEQ ID NO:5 comprising at least 60 nucleotides and a nucleic acid sequence that is 95% homologous to a functional fragment of SEQ ID NO:7 comprising at least 60 nucleotides.

BRIEF DESCRIPTION OF THE FIGURES

FIGS. 1a-1e shows the data indicating induction of robust cellular immune responses following DNA vaccination with EP. Total responses to SIVgag (white bar), env (gray bar), and pol (black bar) after each immunization are shown as stacked group mean responses±SEM. A Tukey post hoc test and a Dunnett T3 post hoc were used to determine the significance of the differences between groups for the third and fourth immunization, respectively.

In FIG. 2a, Dot plots of representative animals are shown. Total SLY proliferative responses are show in the FIG. 2b for $CD4^+$ and in the FIG. 2c $CDS^+$ T cell compartments as stacked group mean responses±SEM. Statistical differences between groups was determined by doing pair-wise Mann-Whitney tests with a Bonferroni adjustment with p values <0.017 being significant.

FIGS. 3a-3d show the polyfunctional profile of SIVpol responses following immunization. PBMCs isolated 2 weeks after the fourth immunization were stimulated in vitro with a SIVpol peptide pool mix for 5 hours. Cells were stained for intracellular production of IFNγ, TNFα and IL-2 and degranulation by CD107a. FIG. 3a shows representative gating analysis for intracellular cytokine staining, The singlet population was discriminated by the use of forward scatter height (FSC-H) and forward scatter area (FSC-A). Subsequently we isolated the lymphocyte population using side scatter area (SSC-A) by FSC-A. Live T cells were identified as negatively staining for a Pacific Blue dump gate, which includes: Violet Vivid Dye for viability, CD14, CD16, and CD19, and positively staining for CD3. Following this, events are sequentially gated on CD8$^+$ and CD4$^+$ events versus IFN-γ to account for down-regulation. In this example the gating for identification of CD8$^+$ T cells is shown. First CD3$^+$ CD8$^+$ T cells are identified by positive CD8 staining and negative CD4 staining, to exclude any CD4$^+$ T cells that may have up-regulated CD8 following activation. CD28 and CD95 staining excluded naïve CD8+ T cells from the analysis. The resulting antigen-experienced CD8$^+$ T cells were then gated for each of the four functions in our panel: CD107a, IL-2, IFNγ, and TNFα. The bar graphs in FIGS. 3a and 3b depict the frequency of each of the 15 functional combinations. FIG. 3b shows CD4$^+$ T cell responses. FIG. 3c shows CD8$^+$ T cell responses. Pie charts show the proportion of SIVpol-specific CD4$^+$ T cells that have 4 functions (purple or dark grey), 3 functions (yellow or light grey), 2 functions (green or medium dark grey) or 1 function (light blue or grey). The number superimposed on the pie charts represent the total frequency of SIVpol responses. FIG. 3d relates to the memory phenotype of IFNγ$^+$ monofunctional CD8$^+$ T cells. Dot plots of IFNα$^-$ monofunctional (dark grey) were overlaid on CD28 by CD95 density plots to determine the memory phenotype of this population. Staining from a representative animal in the DNA+12 group is shown.

FIGS. 4a and 4b show maintenance of polyfunctional memory T cell populations. PBMCs isolated eight months following the final immunization (day of SIVmac251 challenge) were stimulated in vitro with a SIVpol peptide pool mix for 5 hours. Cells were stained for intracellular production of IFNγ, TNFα and IL-2 and degranulation by CD107a. The bar graphs in FIGS. 4a and 4b depict the frequency of each of the 15 functional combinations. FIG. 4a shows CD4$^+$ T cell responses. FIG. 4b shows CD8$^+$ T cell responses. Pie charts show the proportion of SIVpol-specific CD4$^+$ T cells that have 4 functions (purple or dark grey), 3 functions (yellow or light grey), 2 functions (green medium dark grey) or 1 function (light blue or grey). The number superimposed on the pie charts represent the total frequency of SIVpol responses.

FIGS. 5a-5d show data from SIVmac251 mucosal challenge. FIG. 5a shows a comparison of viral loads between vaccinated (or light grey) and unvaccinated (● or dark grey) animals at pre-challenge, week 2 (peak), week 14 (set point), and week 35 (chronic) post-challenge FIG. 5b shows a comparison of pre-challenge, peak, set point and chronic viral loads by group: naïve (● or dark grey), DNA (● or grey), DNA+12 (● or medium dark grey), DNA+RANTES ( or light grey). FIG. 5c shows an Area under the curve plot. Group means are shown. FIG. 5d shows a comparison of viral loads between protective class I alleles, Mamu-B*03 and Mamas-B*017 ( or light grey) and non-controller allele (■ or dark grey) animals during peak, set point, and chronic infection. A two-tailed T test was performed to determine the significance of the differences between groups for FIGS. 5a and 5d and an ANOVA with a two-tailed Dunnett post hoc test was used in FIG. 5b.

FIGS. 6a-6e show CD4$^+$T cell loss following SIVmac251 mucosal challenge. Changes in peripheral CD4$^+$T cell counts following challenge are shown. Relative changes in CD4$^+$T cell counts for each group are depicted in FIG. 6a as percent of baseline counts and group means±SEM are shown for the control (■), DNA (Δ), DNA+12 (∇), and DNA+RANTES (○) groups. Time course of individual CD4$^+$T cell loss following challenge are depicted in FIGS. 6b-6e. Relative changes in CD4$^+$T cell counts for each animal in the Control group are depicted in FIG. 6b as percent of baseline counts. Data for each individual is shown: 4388 (-■-), 4392 (-Δ-), 4396 (-∇-), 4399 (-◇-), 4403 (-●-) and 4406 (-□-). Relative changes in CD4$^+$T cell counts for each animal in the DNA group are depicted in FIG. 6c as percent of baseline counts. Data for each individual is shown: 4387 (-■-) 4411 (-Δ-), 4413 (-∇-), 4416 (-◇-), 4421 (-●-) and 4425 (-□-). Relative changes in CD4$^+$T cell counts for each animal in the DNA+12 group are depicted in FIG. 6d as percent of baseline counts. Data for each individual is shown: 4389 (-■-), 4394 (-Δ-), 4397 (-∇-), 4400 (-◇-), 4404 (-●-) and 4407 (-□-). Relative changes in CD4$^+$T cell counts for each animal in the DNA+RANTES group are depicted in FIG. 6e as percent of baseline counts. Data for each individual is shown: 4408 (-■-), 4410 (-Δ-), 4415 (-∇-), 4417 (-◇-), 4420 (- -) and 4424 (-□-). Animals with haplotypes associated with protection are highlighted in each group. All have the Mamu-B*003 allele with the exception of 4394 in the DNA+12 group which had the Mamu-B*017 allele.

DETAILED DESCRIPTION

Figure 1E:
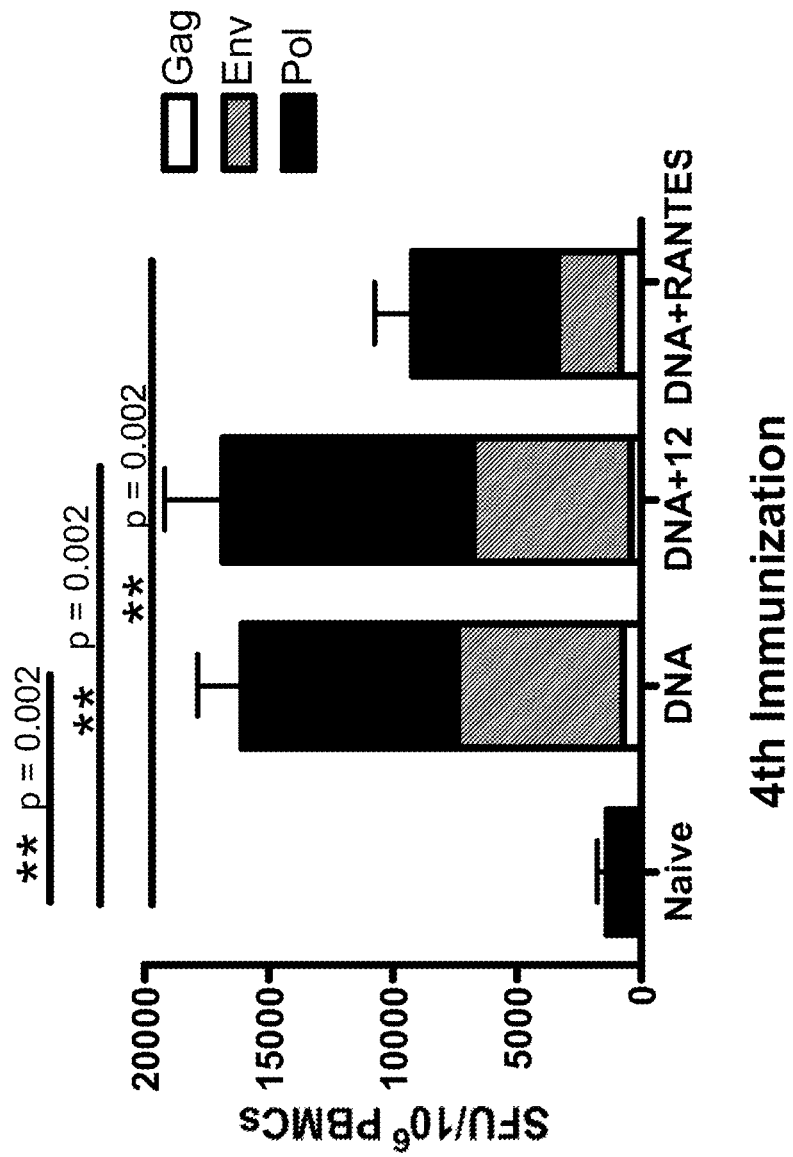

A nucleic acid molecule that encodes human RANTES is provided which has a nucleotide sequence (SEQ ID NO:1) designed to produce high levels of expression in human cells. The amino acid sequences of RANTES encoded by the nucleotide sequence is set forth in SEQ ID NO:2. The nucleotide sequence may be operably linked to regulatory elements necessary for expression in human cells. Additional elements and sequences may be provided to further enhance expression levels. Plasmids, viral vectors or cells comprising SEQ ID NO:1, SEQ ID NO:3, SEQ ID NO:5 or SEQ ID NO:7 may be administered to an individual and expressed in the individual's cells to deliver functional RANTES protein to the individual. In addition, host cells transformed with SEQ ID NO:1, SEQ ID NO:3, SEQ ID NO:5 or SEQ ID NO:7 may be cultured in order to produce RANTES protein.

When delivered as part of an immunotherapeutic or vaccine, nucleic acid molecules that encode RANTES and functional fragments thereof modulate immune responses. Accordingly nucleic acid molecules that encode RANTES and functional fragments thereof may be delivered as immunotherapeutics and/or in combination with or as components of a vaccine that also include nucleic acid molecules that encode an immunogenic target against which an immune response is desired.

While not being bound by scientific theory, an immunotherapeutic useful to modulate immune responses may comprise a nucleic acid molecule comprising SEQ ID NO:1, SEQ ID NO:3, SEQ ID NO:5 or SEQ ID NO:7. A vaccine that can be used to elicit an enhanced immune response against an immunogen may comprise one or more of the following: 1) a nucleic acid molecule comprising SEQ ID NO:1, SEQ ID NO:3, SEQ ID NO:5 or SEQ ID NO:7 and a nucleotide sequence that encodes a target immunogen; and 2) a first nucleic acid molecule comprising SEQ ID NO:1, SEQ ID NO:3, SEQ ID NO:5 or SEQ ID NO:7 and a second nucleic acid molecules comprising a nucleotide sequence that encodes a target immunogen.

Immunotherapeutic and immunization methods can be performed using such nucleic acid molecules. Immunotherapeutics and vaccines can be prepared which have regulatory elements operably linked to SEQ ID NO:1, SEQ ID NO:3, SEQ ID NO:5 or SEQ ID NO:7 in order to achieve a high level of expression of RANTES.

The delivery of a nucleic acid sequence that encodes RANTES or functional fragments thereof to an individual modulates immune responses in the individual. When delivered as an immunotherapeutic, the nucleic acid sequence that encodes RANTES or functional fragments thereof modulates immune responses in the individual to alleviate symptoms or causes of various diseases, conditions and disorders involving the immune system. When delivered to an individual as a component of a vaccine together with a nucleic acid sequence that encodes an immunogen enhances the immune response against the immunogen. When the nucleic acid molecules that encode RANTES or functional fragments thereof are administered to an individual, RANTES is taken up by and expressed in the cells, and the RANTES protein is thereby delivered to the individual. In the case of vaccines, nucleic acid sequences that encode an immunogen are also administered, taken up and expressed by cells whereby the immunogenic protein is produced. Methods of delivering the coding sequences of the proteins may include delivery of a plurality of single nucleic acid molecule or a plurality of multiple different nucleic acid molecules. The coding sequences of the proteins may be for example part of a plasmid, a recombinant vaccine or attenuated vaccine.

Compositions and methods are provided which prophylactically and/or therapeutically immunize an individual against a pathogen or abnormal, disease-related cells. The vaccine may be any type of vaccine such as, a live attenuated vaccine, a recombinant vaccine or a nucleic acid or DNA vaccine. By delivering nucleic acid molecules that encode an immunogen and RANTES or functional fragments thereof, the immune response induced by the vaccine may be modulated. RANTES is particularly useful when delivered via an expressible nucleic acid molecule, such as for example as part of a plasmid or the genome of a recombinant vector or attenuated pathogen or cell. RANTES is particularly useful when delivered prophylactically in order to induce a protective immune response in an uninfected or disease free individual. Nucleic acid molecules encoding RANTES may be delivered in a cell free composition. In some embodiments, nucleic acid molecules encoding RANTES may be administered free of any other cytokine.

Using standard techniques and readily available starting materials, a nucleic acid molecule that encodes RANTES protein may be prepared.

Compositions for delivering the RANTES and methods of using the same as well as vaccines and immunization methods are provided. Compositions comprise nucleic acid molecules that include a nucleotide sequence that encodes RANTES or functional fragment thereof operably linked to regulatory elements. When part of a vaccine, the compositions include a nucleotide sequence that encodes an immunogen operably linked to regulatory elements Injectable pharmaceutical compositions that comprise such compositions may be administered to an individual.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Adjuvant

"Adjuvant" as used herein means any molecule added to the DNA plasmid vaccines described herein to enhance the immunogenicity of the antigens encoded by the DNA plasmids and the encoding nucleic acid sequences described hereinafter.

b. Antibody

"Antibody" as used herein means an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to whom the nucleic acid is administered.

d. Complement

"Complement" or "complementary" as used herein means a nucleic acid can mean Watson-Crick (e.g., A-T/U and C-G) or Hoogsteen base pairing between nucleotides or nucleotide analogs of nucleic acid molecules.

e. Constant Current

"Constant current" as used herein means a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

f. Current Feedback or Feedback

"Current feedback" or "feedback" can be used interchangeably and means the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback can be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop can be instantaneous as it is an analog closed-loop feedback.

g. Decentralized Current

"Decentralized current" as used herein means the pattern of electrical currents delivered from the various needle electrode arrays of the electroporation devices described herein, wherein the patterns minimize, or preferably eliminate, the occurrence of electroporation related heat stress on any area of tissue being electroporated.

h. Electroporation

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

i. Feedback Mechanism

"Feedback mechanism" as used herein means a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism can be performed by an analog closed loop circuit.

j. Functional fragment

"Functional fragment" as used herein with respect to SEQ ID NO:1 refers to a nucleic acid molecule that 1) has a nucleotide sequence corresponding to a portion of SEQ ID NO:1 that is less than the complete SEQ ID NO:1, i.e. excluding the full length SEQ ID NO:1 thereof, and 2) encodes a polypeptide which has RANTES activity, i.e. when expressed in a human, it functions as the RANTES produced when SEQ ID NO:1 is expressed in a human. The size of a function fragments may be 90 or more, 120 or more, 150 or more, 180 or more, 210 or more, or 240 or more in length. DNA fragments can be fewer than 10 nucleotides, fewer than 20, fewer than 30, fewer than 40, fewer than 50, fewer than 60, fewer than 75, fewer than 90, fewer than 120, fewer than 150, fewer than 180, fewer than 210, or fewer than 240. For the purposes of the disclosure herein, it is intended that the sizes set forth herein also constitute the range of sizes such as the size of a function fragments of DNA may be 20-90, 20-120, 20-150, 20-180, 20-210, 20-240, 30-90, 30-120, 30-150, 30-180, 30-210, 30-240, 40-90, 40-120, 40-150, 40-180, 40-210, 40-240, 50-90, 50-120, 50-150, 50-180, 50-210, 50-240, 60-90, 60-120, 60-150, 60-180, 60-210, 60-240, 75-90, 75-120, 75-150, 75-180, 75-210, 75-240, 90-120, 90-150, 90-180, 90-210, 90-240, 20-90, 120-150, 120-180, 120-210, 120-240, 150-180, 150-210, 150-240, 180-210, 180-240 and 210-240 in length.

"Functional Fragment" with respect to polypeptide sequences means a polypeptide encoded by a functional fragment nucleic acid molecule which is a portion of SEQ ID NO:2 that is incomplete, i.e. SEQ ID NO:2 is excluded. The polypeptide fragments may be 30 or more amino acids in length, 35 or more, 40 or more, 45 or more, 50 or more, 55 or more, 60 or more, 65 or more, 70 or more, 75 or more, 80 or more, 85 or more, or 90 or more in length. Polypeptide fragments can be fewer than 10 amino acids, fewer than 15, fewer than 20, fewer than 25, fewer than 30, fewer than 35, fewer than 40, fewer than 45, fewer than 50, fewer than 55, fewer than 60, fewer than 65, fewer than 70, fewer than 75, fewer than 80, fewer than 85 or fewer than 90 amino acids in length. For the purposes of the disclosure herein, it is intended that the sizes set forth herein also constitute the range of sizes such as the size of a function fragments of protein may be 30-35, 30-40, 30-45, 30-50, 30-55, 30-60, 30-65, 30-70, 30-75, 30-80, 30-85, 30-90, 35-40, 35-45, 35-50, 35-55, 35-60, 35-65, 35-70, 35-75, 35-80, 35-85, 35-90, 40-45, 40-50, 40-55, 40-60, 40-65, 40-70, 40-75, 40-80, 40-85, 40-90, 45-50, 45-55, 45-60, 45-65, 45-70, 45-75, 45-80, 45-85, 45-90, 50-55, 50-60, 50-65, 50-70, 50-75, 50-80, 50-85, 50-90, 55-60, 55-65, 55-70, 55-75, 55-80, 55-85, 55-90, 60-65, 60-70, 60-75, 60-80, 60-85, 60-90, 65-70, 65-75, 65-80, 65-85, 65-90, 70-75, 70-80, 70-85, 70-90, 75-80, 75-85, 75-90, 80-85, 85-90 and 85-90 in length.

k. Genetic construct

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

l. Identical

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

m. Impedance

"Impedance" can be used when discussing the feedback mechanism and can be converted to a current value according to Ohm's law, thus enabling comparisons with the preset current.

n. Immune Response

"Immune response" as used herein means the activation of a host's immune system, e.g., that of a mammal, in response to the introduction of antigen such as an influenza hemagglutinin consensus antigen. The immune response can be in the form of a cellular or humoral response, or both.

o. Nucleic Acid

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

p. Operably Linked

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

q. Promoter

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

r. Stringent Hybridization Conditions

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

s. Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or more nucleotides or 8, 9, 10, 11, 12, 13, 14, 15, 16, 17, 18, 19, 20, 21, 22, 23, 24, 25, 30, 35, 40, 45, 50, 55, 60, 65, 70, 75, 80, 85 or 90 or more amino acids, or that the two sequences hybridize under stringent hybridization conditions.

t. Substantially Identical

"Substantially identical" as used herein means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or more nucleotides or 8, 9, 10, 11, 12, 13, 14, 15, 16, 17, 18, 19, 20, 21, 22, 23, 24, 25, 30, 35, 40, 45, 50, 55, 60, 65, 70, 75, 80, 85 or 90 or more amino acids, or with respect to nucleic acids, if the first sequence is substantially complementary to the complement of the second sequence.

u. Variant

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

v. Vector

"Vector" as used herein means a nucleic acid sequence containing an origin of replication. A vector can be a vector, bacteriophage, bacteria, artificial chromosome or yeast artificial chromosome. A vector can be a DNA or RNA vector. A vector can be a self-replicating extrachromosomal vector, and preferably, is a DNA plasmid.

2. Rantes

RANTES is encoded by SEQ ID NO:1. The sequence may further comprise one or more additional amino acid sequence elements. For example the RANTES encoded by the nucleic acid sequence may further comprise on its N-terminal an IgE or IgG leader amino acid sequence. The IgE leader amino acid sequence may be SEQ ID NO:3. Likewise, coding sequences encoding IgE or IgG leader sequences may be linked to the coding sequences encoding the immunogen.

SEQ ID NO:1 is optimized for high levels of expression. The nucleic acid sequence may comprise a Kozak sequence in the 5' untranslated region. The nucleic acid sequence may further comprise nucleic acid sequences that encode a leader sequence. The coding sequence of an N terminal leader sequence is 5' of the RANTES coding sequence. The N-terminal leader can facilitate secretion. The N-terminal leader can be an IgE leader or an IgG leader. SEQ ID NO:3 is the same RANTES coding sequence as disclosed in SEQ ID NO:1 further comprising coding sequences for IgE; leader sequence linked to the RANTES protein at the N terminal. The nucleic acid sequence may comprise a Kozak sequence in the 5' untranslated region. SEQ ID NO:5 is the same IgE leader-RANTES coding sequence as disclosed in SEQ ID NO:3 and further comprising a Kozak sequence in the 5' untranslated region.

3. Genetic Constructs and Plasmids

Provided herein are genetic constructs that can comprise a nucleic acid sequence that encodes RANTES or a functional fragment thereof. The genetic construct can be present in the cell as a functioning extrachromosomal molecule comprising the nucleic acid encoding the RANTES or a functional fragment thereof. The genetic construct comprising the nucleic acid encoding RANTES or a functional fragment thereof can be linear minichromosome including centromere, telomers or plasmids or cosmids.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of RANTES or a functional fragment thereof. The regulatory elements can be a promoter, an enhancer an initiation codon, a stop codon, or a polyadenylation signal.

Compositions may comprise a first nucleic acid sequence which encodes RANTES or a functional fragment thereof, and may further comprise one or more additional nucleic acid sequence(s) that encodes one or more immunogens. The first and additional nucleic acid sequences may be present on the same nucleic acid molecule or different nucleic acid molecules. The first and additional nucleic acid sequences can be under the control of regulatory elements that function in a human cell.

The nucleic acid sequences may make up a genetic construct that can be a vector. The vector can be capable of expressing RANTES or a functional fragment thereof in the cell of an individual in a quantity effective to elicit an immune response in the individual. The vector can be recombinant. The vector can comprise heterologous nucleic acid encoding RANTES or a functional fragment thereof. The vector can be a plasmid. The vector can be useful for transfecting cells with nucleic acid encoding RANTES or a functional fragment thereof, which the transformed host cell is cultured and maintained under conditions wherein expression of the RANTES or a functional fragment thereof takes place.

The vector can comprise heterologous nucleic acid encoding RANTES or a functional fragment thereof and can further comprise an initiation codon, which can be upstream of the RANTES or a functional fragment thereof coding sequence, and a stop codon, which can be downstream of the RANTES or a functional fragment thereof coding sequence. The initiation and termination codon can be in frame with the RANTES or a functional fragment thereof coding sequence. The vector can also comprise a promoter that is operably linked to the RANTES or a functional fragment thereof coding sequence. The promoter operably linked to the RANTES or a functional fragment thereof coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the RANTES or a functional fragment thereof coding sequence. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the RANTES or a functional fragment thereof coding sequence. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962, 428, and WO94/016737, the contents of each are fully incorporated by reference.

The vector can also comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The backbone of the vector can be pAV0242. The vector can be a replication defective adenovirus type 5 (Ad5) vector.

The vector can also comprise a regulatory sequence, which can be well suited for gene expression in a human cell into which the vector is administered. The RANTES or a functional fragment thereof coding sequence allow more efficient transcription of the coding sequence in the host cell. The vector can be expression vectors or systems to produce protein by routine techniques and readily available starting materials including Sambrook et al., Molecular Cloning A Laboratory Manual, Second Ed., Cold Spring Harbor (1989), which is incorporated fully by reference.

The genetic constructs and components disclosed herein with respect to RANTES or a functional fragment thereof may also be designed with coding sequences that encode an immunogen rather than RANTES or a functional fragment thereof whereby such constructs would together with nucleic acid sequence that encode RANTES or a functional fragment thereof provide an improved vaccine that induces immune responses against the immunogen.

4. Pharmaceutical Compositions

Provided herein are pharmaceutical compositions according to the present invention which comprise about 1 nanogram to about 10 mg of DNA. In some embodiments, pharmaceutical compositions according to the present invention comprise from between: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg. In some embodiments, pharmaceutical compositions according to the present invention comprise about 5 nanogram to about 10 mg of DNA. In some embodiments, pharmaceutical compositions according to the present invention comprise about 25 nanogram to about 5 mg of DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. In some embodiments, the pharmaceutical compositions comprise about 10 microgram to about 100 micrograms of DNA. In some embodiments, the pharmaceutical compositions comprise about 20 micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about 35 nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

Provided herein is an immunotherapeutic capable of modulating an immune response in a human. The immunotherapeutic can comprise a genetic construct as discussed above which includes SEQ ID NO:1, SEQ ID NO:3, SEQ ID NO:5, SEQ ID NO:7 or a functional fragment thereof.

Provided herein is a vaccine capable of generating in a human an immune response against one or more immunogens. The vaccine can comprise the genetic construct as discussed above which includes SEQ ID NO:1, SEQ ID NO:3, SEQ ID NO:5 or SEQ ID NO:7 or a functional fragment thereof in combination with a genetic construct as discussed above which includes a nucleic acid sequence that encodes an immunogen. The genetic construct encoding RANTES or a fragment thereof may be on the same or a different nucleic acid molecule as the genetic construct which includes a nucleic acid sequence that encodes an immunogen.

The immunotherapeutic or vaccine may be a plasmid DNA composition. The plasmid DNA composition may comprise a plurality of the same or different plasmids comprising one or more of genetic constructs. The plasmid DNA composition may comprise the nucleic acid sequence that encode RANTES or a functional fragment thereof. When it is a vaccine it may further comprise, on the same or different plasmid, nucleic acid sequence that encodes an immunogen.

DNA vaccine technology which can be used to generate the DNA plasmid compositions useful as immunotherapeutics or vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

Recombinant viral vectors comprising the genetic construct described above may also be produced. The recombinant viral vector can also comprise SEQ ID NO:1, SEQ ID NO:3, SEQ ID NO:5, SEQ ID NO:7 or a functional fragment thereof with or without a genetic construct which includes a nucleic acid sequence that encodes an immunogen. SEQ ID NO:1, SEQ ID NO:3, SEQ ID NO:5, SEQ ID NO:7 or a functional fragment thereof may be incorporated into an attenuated vaccine such as an attenuated live vaccines, killed vaccines and vaccines that use recombinant vectors to deliver foreign genes. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freund's incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LOS), or lipid. The transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA plasmid compositions can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be an adjuvant. The adjuvant may be other genes that are expressed in alternative plasmid or are delivered as proteins in combination with the plasmid above. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant may be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which may be useful adjuvants include those encoding: MCP-1, MIP-1α, MIP-1p, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The plasmid compositions can further comprise a genetic vaccine facilitator agent as described in U.S. Ser. No. 021,579 filed Apr. 1, 1994, which is fully incorporated by reference.

5. Methods of Delivery

Provided herein is a method for delivering the pharmaceutical formulations, for providing genetic constructs that encode RANTES or a fragment thereof with or without genetic constructs that which comprise coding sequences for immunogens against which an immune response is desired. The method of delivering the pharmaceutical formulation can be provided to modulate an individual's immune system or to induce a therapeutic and/or prophylactic immune response against a specific immunogen.

Compositions can be delivered in the form as described in U.S. Pat. Nos. 4,945,050 and 5,036,006, which are both incorporated fully by reference.

a. Routes of Administration

The compositions can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. The composition can be administered by traditional syringes, needleless injection devices, "microprojectile bombardment gone guns", or other physical methods such as electroporation ("EP"), "hydrodynamic method", or ultrasound.

The vector of the composition can be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia.

b. Electroporation

Administration of the DNA via electroporation of the plasmids of the vaccine may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA® EP system (VGX Pharmaceuticals, Blue Bell, Pa.) or Elgen electroporator (Genetronics, San Diego, Calif.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Aldi, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application, Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

c. Method of Preparing Plasmids

Provided herein is methods for preparing the DNA plasmids that comprise SEQ ID NO:1 discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

6. Immunogens

The present invention may be used to immunize an individual against pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, listeria and shigella. In addition, the present invention is also useful to immunize an individual against protozoan pathogens that include a stage in the life cycle where they are intracellular pathogens. Table 1 provides a listing of some of the viral families and genera for which vaccines according to the present invention can be made. DNA constructs that comprise DNA sequences that encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

TABLE 1

| Viruses |
|---|
| Picornavirus Family |
| Genera: |
| Rhinoviruses: (Medical) responsible for -50% cases of the common cold. |
| Etheroviruses: (Medical) includes polioviruses, coxsackieviruses, echoviruses, and human enteroviruses such as hepatitis A virus. |
| Apthoviruses: (Veterinary) these are the foot and mouth disease viruses. |
| Target antigens: VP1, VP2, VP3, VP4, VPG |
| Calcivirus Family |
| Genera: |
| Norwalk Group of Viruses: (Medical) these viruses are an important causative agent of epidemic gastroenteritis. |
| Togavirus Family |
| Genera: |
| Alphaviruses: (Medical and Veterinary) examples include Sindbis virus, RossRiver virus and Venezuelan Eastern & Western Equine encephalitis viruses. |
| Reovirus: (Medical) Rubella virus. |
| Flariviridae Family |
| Examples include: (Medical) dengue, yellow fever, Japanese encephalitis, St. Louis encephalitis and tick borne encephalitis viruses. West Nile virus (Genbank NC001563, AF533540, AF404757, AF404756, AF404755, AF404754, AF404753, AF481864, M12294, AF317203, AF196835, AF260969, AF260968, AF260967, AF206518 and AF202541) |
| Representative Target antigens: E NS5 C |
| Hepatitis C Virus: (Medical) |
| these viruses are not placed in a family yet but are believed to be either a togavirus or a flavivirus. Most similarity is with togavirus family. |
| Coronavirus Family: (Medical and Veterinary) |
| Infectious bronchitis virus (poultry) |
| Porcine transmissible gastroenteric virus (pig) |
| Porcine hemagglutinating encephalomyelitis virus (pig) |
| Feline infectious peritonitis virus (cats) |
| Feline enteric coronavirus (cat) |
| Canine coronavirus (dog) |
| SARS associated coronavirus |
| The human respiratory coronaviruses cause about 40% of cases of common cold. EX. 224E, OC43 Note—coronaviruses may cause non-A, B or C hepatitis |
| Target antigens: E1—also called M or matrix protein |
| E2—also called S or Spike protein |
| E3—also called BE or hemagglutin-elterose glycoprotein (not present in all coronaviruses) |
| N—nucleocapsid |
| Rhabdovirus Family |
| Genera: |
| Vesiculovirus, Lyssavirus: (medical and veterinary) rabies |
| Target antigen: G protein, N protein |
| Filoviridae Family: (Medical) |
| Hemorrhagic fever viruses such as Marburg and Ebola virus |

TABLE 1-continued

Viruses

Paramyxovirus Family:
  Genera:
  Paramyxovirus: (Medical and Veterinary)
  Mumps virus, New Castle disease virus (important pathogen
  in chickens)
  Morbillivirus: (Medical and Veterinary) Measles, canine distemper
  Pneumovirus: (Medical and Veterinary) Respiratory syncytial virus
Orthomyxovirus Family (Medical)
  The Influenza virus
Bunyavirus Family
  Genera:
  Bunyavirus: (Medical) California encephalitis, La Crosse
  Phlebovirus: (Medical) Rift Valley Fever
  Hantavirus: Puremala is a hemahagin fever virus
  Nairvirus (Veterinary) Nairobi sheep disease
  Also many unassigned bungaviruses
Arenavirus Family (Medical)
  LCM, Lassa fever virus
Reovirus Family
  Genera:
  Reovirus: a possible human pathogen
  Rotavirus: acute gastroenteritis in children
  Orbiviruses: (Medical and Veterinary)
  Colorado Tick fever, Lebombo (humans) equine
  encephalosis, blue tongue
Retroyirus Family
  Sub-Family:
  Oncorivirinal: (Veterinary) (Medical) feline leukemia
  virus, HTLVI and HTLVII
  Lentivirinal: (Medical and Veterinary) HIV, feline
  immunodeficiency virus, equine infections, anemia virus
Spumavirinal Papovavirus Family
  Sub-Family:
  Polyomaviruses: (Medical) BKU and JCU viruses
  Sub-Family:
  Papillomavirus: (Medical) many viral types associated
  with cancers or malignant progression of papilloma.
Adenovirus (Medical)
  EX AD7, ARD., O.B. - cause respiratory disease - some
  adenoviruses such as 275 cause enteritis
Parvovirus Family (Veterinary)
  Feline parvovirus: causes feline enteritis
  Feline panleucopeniavirus
  Canine parvovirus
  Porcine parvovirus
Herpesvirus Family
  Sub-Family:
  alphaherpesviridue
  Genera:
  Simplexvirus (Medical)
  HSVI (Genbank X14112, NC001806), HSVII (NC001798)
  Varicella zoster: (Medical Veterinary)
  Pseudorabies
  varicella zoster
  Sub-Family
  betaherpesviridae
  Genera:
  Cytomegalovirus (Medical)
  HCMV
  Muromegalovirus
  Sub-Family.
  Gammaherpesviridae
  Genera:
  Lymphocryptovirus (Medical)
  EBV - (Burkitt's lymphoma)
Poxvirus Family
  Sub-Family:
  Chordopoxviridue (Medical - Veterinary)
  Genera:
  Variola (Smallpox)
  Vaccinia (Cowpox)
  Parapoxivirus - Veterinary
  Auipoxvirus - Veterinary
  Capripoxvirus
  Leporipoxvirus
  Suipoxviru's
  Sub-Family:
  Entemopoxviridue TABLE 1-continued Viruses Hepadnavirus Family
  Hepatitis B virus
  Unclassified Hepatitis delta virus

TABLE 2

Bacterial pathogens
  Pathogenic gram-positive cocci include: pneumococcal;
  staphylococcal; and streptococcal. Pathogenic gram-negative cocci
  include: meningococcal; and gonococcal.
  Pathogenic enteric gram-negative bacilli include: enterobacteriaceae;
  *pseudomonas*, acinetobacteria and *eikenella*, melioidosis; *salmonella*;
  shigellosis; hemophilus; chancroid; brucellosis; tularemia; *yersinia*
  (*pasteurella*); *streptobacillus mortiliformis* and *spirillum*; *listeria
  monocytogenes*; *erysipelothrix rhusiopathiae*; diphtheria, cholera,
  anthrax; donovanosis (granuloma inguinale); and bartonellosis.
  Pathogenic anaerobic bacteria include: tetanus; botulism; other
  clostridia; tuberculosis; leprosy; and other mycobacteria. Pathogenic
  spirochetal diseases include: syphilis; -treponematoses: yaws, pinta
  and endemic syphilis; and leptospirosis.
  Other infections caused by higher pathogen bacteria and pathogenic
  fungi include: actinomycosis; nocardiosis; cryptococcosis,
  blastomycosis, histoplasmosis and coccidioidomycosis; candidiasis,
  aspergillosis, and mucormycosis; sporotrichosis;
  paracoccidiodomycosis, petriellidiosis, torulopsosis, mycetoma, and
  chromomycosis; and dermatophytosis.
  Rickettsial infections include rickettsial and rickettsioses.
  Examples of mycoplasma and chlamydial infections include:
  mycoplasma pneurnoniae; lymphogranuloma venereum;
  psittacosis; and perinatal chlamydial infections.
  Pathogenic eukaryotes
  Pathogenic protozoans and helminths and infections thereby include:
  amebiasis; malaria; leishmaniasis; trypanosomiasis; toxoplasmosis;
  pneumocystis carinii; babesiosis; giardiasis; trichinosis; filariasis;
  schistosomiasis; nematodes; trematodes or flukes; and cestode
  (tapeworm) infections.

Another aspect of the present invention provides a method of conferring a protective immune response against hyperproliferating cells that are characteristic in hyperproliferative diseases and to a method of treating individuals suffering from hyperproliferative diseases. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. To immunize against hyperproliferative diseases, a genetic construct that includes a nucleotide sequence that encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides; which comprise at least an epitope found on such proteins. In some cases, a hyperproliferative-associated protein is the product of a mutation of a gene that encodes a protein. The mutated gene encodes a protein that is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anticancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins that are found at higher levels in tumor cells including the protein recognized by monoclonal antibody 17-IA and folate binding proteins or PSA.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

In treating or preventing cancer, embodiments which are free of cells are particularly useful.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases.

Vaccination against the variable region of the T cells would elicit an immune response including CTLs to eliminate those T cells.

In RA, several specific variable regions of T cell receptors (TCRs) that are involved in the disease have been characterized. These TCRs include V.beta.-3, V.beta.-14, 20 V.beta.-17 and Va-17. Thus, vaccination with a DNA construct that encodes at least one of these proteins will elicit an immune response that will target T cells involved in RA. See: Howell, M. D., et al., 1991 Proc. Nat. Acad. Sci. USA 88:10921-10925; Piliard, X., et al, 1991 Science 253:325-329; Williams, W. V., et al., 1992 J Clin. Invest. 90:326-333; each of which is incorporated herein by reference. In MS, several specific variable regions of TCRs that are involved in the disease have been characterized. These TCRs include VfP and Va-10. Thus, vaccination with a DNA construct that encodes at least one of these proteins will elicit an immune response that will target T cells involved in MS. See: Wucherpfennig, K. W., et al., 1990 Science 248:1016-1019; Oksenberg, J. R., et al, 1990 Nature 345:344-346; each of which is incorporated herein by reference.

In scleroderma, several specific variable regions of TCRs that are involved in the disease have been characterized. These TCRs include V.beta.-6, V.beta.-8, V.beta.-14 and Va-16, Va-3C, Va-7, Va-14, Va-15, Va-16, Va-28 and Va-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies that bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al 1987 Sequence of Proteins of Immunological Interest U.S. Department of Health and Human Services, Bethesda Md., which is incorporated herein by reference. In addition, a general method for cloning functional variable regions from antibodies can be found in Chaudhary, V. K., et al, 1990 Proc. Natl. Acad Sci. USA 87:1066, which is incorporated herein by reference.

In addition to using expressible forms of immunomodulating protein coding sequences to improve genetic vaccines, the present invention relates to improved attenuated live vaccines and improved vaccines that use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference.

Gene constructs are provided which include the nucleotide sequence that encodes an IL-28 or functional fragments thereof, wherein the nucleotide sequence is operably linked to regulatory sequences that can function in the vaccine to effect expression. The gene constructs are incorporated in the attenuated live vaccines and recombinant vaccines to produce improved vaccines according to the invention.

The present invention provides an improved method of immunizing individuals that comprises the step of delivering gene constructs to the cells of individuals as part of vaccine compositions which include DNA vaccines, attenuated live vaccines and recombinant vaccines. The gene constructs comprise a nucleotide sequence that encodes an IL-28 or functional fragments and that is operably linked to regulatory sequences that can function in the vaccine to effect expression. The improved vaccines result in an enhanced cellular immune response.

EXAMPLES

Example 1

The present invention is further illustrated in the following Example. It should be understood that this Example, while indicating preferred embodiments of the invention, are given by way of illustration only. From the above discussion and this Example, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Introduction

The cellular immune response induced by electroporation (EP) of optimized, consensus SIVmac plasmid constructs expressing SIVgag, env, and poi was evaluated and compared to cellular immune response induced by electroporation (EP) of the optimized, consensus SIVmac plasmid constructs in combination with-EP of a plasmid-expressing rhesus IL-12 or RANTES could alter the magnitude and quality of the cellular immune response. Profound improvement in T cell immune responses as measured by ELISpot, polyfunctional flow analysis was observed, ex vivo proliferation as well as epitope breadth. An assessment of the impact of these vaccination approaches on viral loads in an unmatched, SIVmac251 intrarectal challenge was also done. DNA vaccination alone was found to impact a viral challenge in this study and protect against CD4 T cell loss. The co-delivery of plasmid IL-12 and RANTES resulted in an enhanced control of viral replication. Thus, manipulating both the delivery and design of plasmid vaccine cassette appear to be important for the generation of high frequency cellular immune responses of relevance to HIV model systems.

Materials and Methods

Animals.

Chinese-origin rhesus macaques (*Macaca mulatta*) were housed at BIOQUAL, Inc. (Rockville, Md.), in accordance with the standards of the American Association for Accreditation of Laboratory Animal Care. Animals were allowed to acclimate for at least 30 days in quarantine prior to any experimentation.

Immunization.

A group of six rhesus macaques (DNA) were immunized at weeks 0, 8, 12 and 24 with 1.5 mg each of SIVgag, SIVenv and SIVpol. The DNA at each immunization time point was delivered into a single site in the quadriceps muscle followed by in vivo EP. Another two groups of six macaques were immunized at weeks 0, 8, and 12 with 1.5 mg each of SIVgag, SIVenv, SIVpol and rhesus IL-12 (DNA+12) or RANTES (DNA+RANTES). Plasmid adjuvants were excluded from the 4$^{th}$ immunization (week 24) in the DNA+12 and DNA+RANTES groups. Six macaques were immunized with sterile water for injection as a negative control (Naive). All EP procedures were performed using the constant current CELLECTRA® device (VGX Pharmaceuticals, The Woodlands, Tex.). EP conditions were 0.5 Amps, 3 pulses, 52 msec pulse length with 1 sec between pulses.

Blood Collection.

Animals were bled every two weeks for the duration of the study. Ten ml of blood were collected in EDTA tubes. Peripheral blood mononuclear cells (PBMC) were isolated by standard Ficoll-hypaque centrifugation and resuspended in complete culture medium (RPMI 1640 with 2 mM L-glutamine supplemented with 10% heat-inactivated fetal bovine serum, 100 IU/ml penicillin, 100 µg/ml streptomycin, and 55 µm β-mercaptoethanol.) RBCs were lysed with ACK lysis buffer (Cambrex Bio Science, East Rutherford, N.J.).

Plasmids and Plasmid Products.

The plasmids used in this study express the modified consensus antigens for SIVgag (pSIVgag), SIVpol (pSIVpol) or SIVenv (pSIVenv). To improve expression, an efficient IgE leader sequence was included. In addition, SIV env V1 and V2 regions were shortened by removing N-linked glycosylation sites and the cytoplasmic tail was truncated to prevent envelope recycling. For SIV pol, 3 mutations were introduced to deactivate the protease, reverse transcriptase, and RNAse H. The resulting optimized SIV DNA immunogens were codon- and RNA-optimized, synthesized, and cloned into the pVAXI expression vector to create optimized expression constructs for SIVgag (pSIVgag), SIVenv (pSIVenv), and SIVpol (pSIVpol). These plasmid constructs were then manufactured at the 10 L scale (VGXI, Inc., The Woodlands, Tex.), and formulated for use in the studies described here. Purified plasmid DNA was formulated in 0.15M citrate buffer pH 6.7 with 0.25% bupivacaine in water.

Peptides.

Reagents were obtained through the AIDS Research and Reference Reagent Program, Division of AIDS, NIAID, NIH: SIVmac239 gag peptides (#6204), SIVmac239 env peptides (#6883), and SIVmac239 pol peptides (#6443).

Carboxyfluorescein Succinimidyl Ester (CFSE) Conjugation and Flow Cytometry Analysis of PBMCs.

CFSE was performed on fresh PBMCs isolated two weeks following the fourth immunization as previously described.

Enzyme Linked Immunospot Assay (ELISpot).

ELISpots were performed as previously described, using a monkey IFNγ ELISpot kit (Mabtech, Cincinnati, Ohio). The input cell number for the first two immunizations was $2 \times 10^5$ cells. For third and fourth immunization time points, the input cell number was decreased to $1 \times 10^5$ cells due to excessive spot number. The mean number of spots from triplicate wells was adjusted to reflect the number of spots per $10^6$ PBMC. The SIV-specific responses were calculated after subtraction of spots formed in response to culture medium alone from the value of spots formed in response to each of the SIV peptide pools used for stimulation. Responses that were ≥50 SFU/$10^6$ PBMCs and greater than 2× the medium alone response were considered positive and the net values were then added.

SIVpol Epitope Matrix Mapping.

The SIVpol peptide library was divided into 33 pools using a matrix format, as previously described, and used to stimulate cryo-preserved PBMCs isolated after the fourth immunization. The breadth of the response was assessed using the IFNγ ELISpot assay. Estimates of the maximum number of epitopes were based on the total number of recognized peptides. The estimates of the minimum number of epitopes were calculated by dividing the number of positive peptide runs, a series of two or more consecutive positive peptides, by three and rounding up to the nearest integer.

Intracellular Cytokine Staining.

Polyfunctional T cell analysis was performed on fresh PBMCs isolated 2 weeks after the fourth immunization and eight months following the final immunization as previously described. Data are reported after background correction. Positive responses were defined as greater than 0.05%.

Cryo-preserved PBMCs were quick thawed and rested overnight at 37° C. in complete media before stimulation. CCR5 (BD Biosciences,) expression was measured on antigen-specific CD8 T cells for each function as well as the total functional response. Both the IFNγ and TNFα antibodies were on Alexa Fluor 700 to accommodate additional stains in this panel. Data are reported after background correction and shown as a percentage of the total CD8 population.

SIVmac251 Challenge.

Animals were challenged eight months following the fourth immunization with 25 monkey infectious doses (MID) of SIVmac251 by the intrarectal route. Viral stocks were prepared by Ronald Desrosiers and provided by Advanced BioSciences Laboratories, Inc (ABL, Inc.) (Kensington, Md.) and titered by BIOQUAL, Inc. (Rockville, Md.).

Quantitative Nucleic Acid Sequence Based Amplification (NASBA) Assay for Plasma Viral Load.

Plasma viral load was determined by quantitative NASBA assay for SIVgag by ABL Inc. as previously described.

MHC Class I Genotyping

Comprehensive sequence based MHC-I genotyping was performed using a combination of Sanger sequencing and pyrosequencing methods as previously described. Briefly, total cellular RNA was isolated from PBMC using the MagNA Pure LC RNA Isolation Kit (Roche Applied Sciences, Indianapolis, Ind.). cDNA was generated from RNA using the SuperscriptIII First-Strand Synthesis System (Invitrogen, Carlsbad, Calif.) and used as a template for PCR amplification with Phusion High-Fidelity Polymerase (New England BioLabs, Ipswich, Mass.) and MHC-I specific primers. PCR products were gel purified using the MinElute Gel Extraction Kit (Qiagen, Valencia, Calif.). For Sanger sequencing, these products were cloned into bacteria using the Zero Blunt TOPO PCR Cloning Kit with TOP 10 Chemically Competent *E. coli* (Invitrogen, Carlsbad, Calif.). 96-192 transformed bacterial colonies per animal were grown overnight in LB+50 ug/ml kanamycin; plasmid DNA was subsequently isolated using the Perfectprep Plasmid 96 Vac Bind Kit (5 PRIME, Gaithersburg, Md.). Sanger sequencing reactions covering the highly variable peptide-binding domain encoded by MHC-I exons 2 & 3 were performed using sequence-specific PCR primers with the DYEnamic ET Terminator Cycle Sequencing Kit (GE Healthcare, Piscataway, N.J.), and analyzed using an Applied Biosystems 3730×1 Genetic Analyzer (Applied Biosystems, Foster City, Calif.). A subset of 5 animals was also genotyped using Roche/454-pyrosequencing of a universal diagnostic 190 bp PCR amplicon in MHC-1 exon 2. This amplicon was amplified from cDNA, gel purified, quantified, normalized, and pooled and run on a Genome Sequencer FLX instrument at the 454 Sequencing Center (454 Life Sciences, Branford, Conn.) or at the University of Illinois at Urbana-Champaign High-Throughput Sequencing Center (Urbana, Ill.). Sequence analysis was performed using CodonCode aligner (CodonCode Corporation, Deham, Mass.) and Lasergene 8 (DNA Star, Madison, Wis.). Assembled contigs were compared to an in-house database of known rhesus macaque MHC-I alleles using BLASTN.

Statistics.

For comparisons of IFNγ ELISpots, T cell proliferation, and cytokine production two tailed Mann-Whitney tests or One-Way ANOVA with Tukey or Dunnett T3 post hoc tests were performed when appropriate using SPSS 17.0 Statistical Software. Viral loads were log-transformed to normalize the data before statistical analysis. P values that were <0.05 were considered significant.

Results

Study Design

Twenty-four Chinese rhesus macaques were divided into four immunization groups (Table 3). Group 1 (DNA) received optimized plasmids encoding SIVgag, SIVenv and SIVpol. Group 2 (DNA+12) received plasmid encoded rhIL-12 and Group 3 (DNA+RANTES) received plasmid encoded RANTES in addition to the SIV plasmids. Group 4 (Naïve) received saline injections. Plasmids were administered at a dose of 1.5 mg/construct/immunization at weeks 0, 8, 12, and 24. Monkeys were immunized by intramuscular injection followed by in vivo EP.

DNA Plasmid Delivery with Electroporation Induces Robust, Highly Proliferative Cellular Immune Responses.

First, the induction of the cellular immune response in each animal was evaluated by IFNγ ELISpot. PBMCs isolated two weeks after each immunization were assayed for SIV specific IFNγ production. Co-immunization of plasmid rhIL-12 resulted in a nine-fold increase in ELISpot number compared to DNA alone after the first vaccination (60±49 and 569±248 SFU/$10^6$ PBMCs, respectively). This early enhancement diminished with further immunizations. Boosting of cellular responses was observed following each of the four immunizations culminating in robust anti-SIV IFNγ ELISpots that averaged 16,000 SFU/$10^6$ PBMCs, or 1.6% of the PBMC population (FIGS. 1a-1e). The DNA+RANTES group exhibited consistently lower ELISpot responses especially following the third immunization when they were significantly lower than the DNA (p<0.001) and DNA+12 (p=0.001) groups. After four immunizations the DNA+RANTES group had a total IFNγ response of 9,217±2111 SFU/$10^6$ PBMCs.

Examination of the SIVpol-specific IFNγ response after the fourth immunization revealed that all three groups had a large breadth of response that covered the entire immunogen (Table 4). Given that one epitope could potentially be represented in 3 peptides based on an overlap of 11 amino acids, the epitope number would be roughly one third of the total number of peptides represented in the positive pools. Interestingly, the DNA+RANTES group, despite having a lower magnitude of SIVpol responses than the other vaccination groups, had the most diverse response which recognized an estimated 68±3.67 epitopes.

Figure 2A:
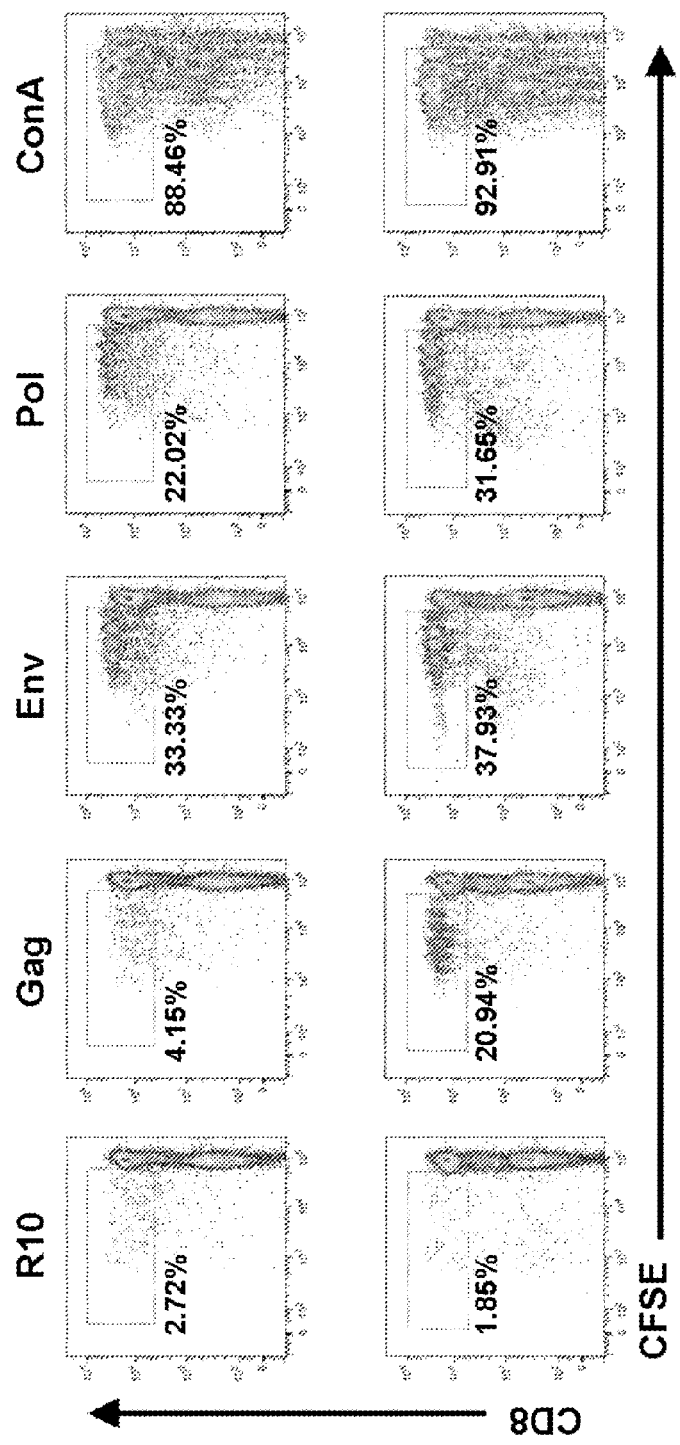
FIGS. 2a-2c show ex-vivo proliferative capacity following DNA immunization. Fresh PBMCs isolated two weeks following the fourth immunization were stained with CFSE and stimulated with SIVgag (white bar), env (gray bar), and pol (black bar) peptides in vitro for 5 days to determine the proliferative capacity of antigen-specific cells.
Figure 2B:
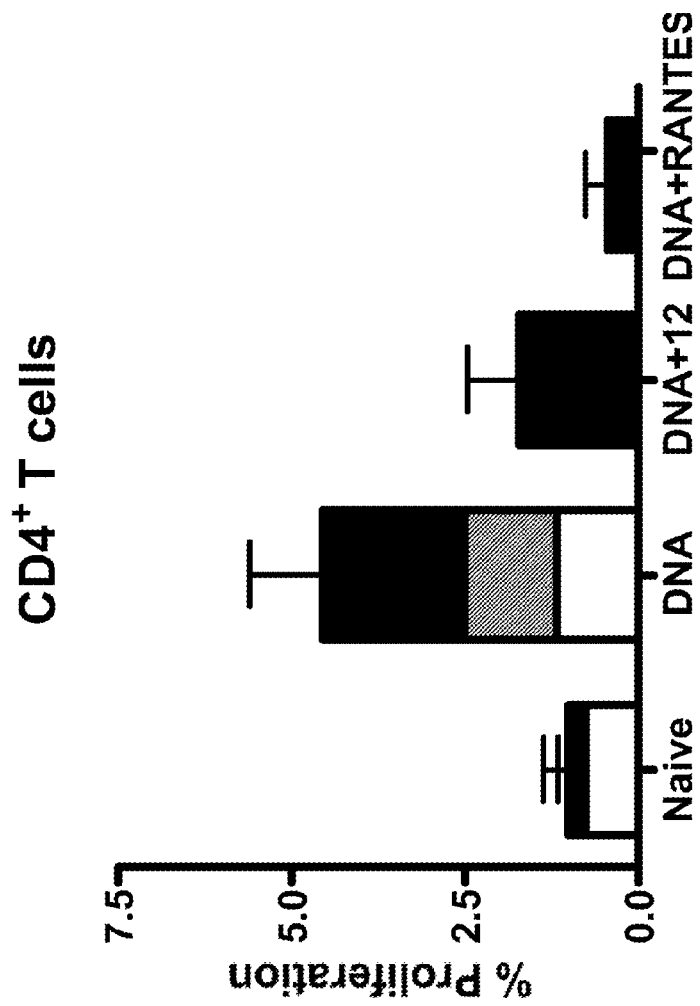
Figure 2C:
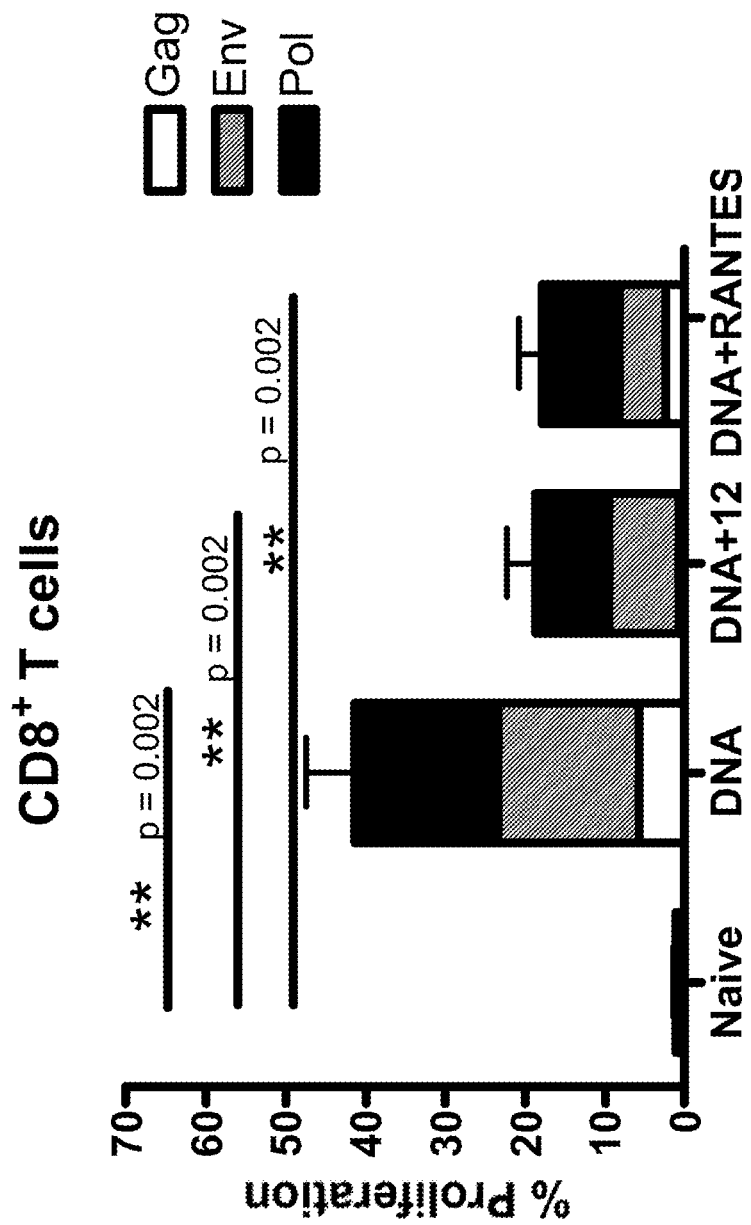

Next, the proliferative capacity of the vaccine induced CD4$^+$ and CD8$^+$ T cell responses was assessed using the CFSE proliferation assay (FIG. 2a). The DNA group had CD4$^+$ T cell proliferative responses that were higher than the DNA+12 and DNA+RANTES groups (4.56±2.72% and 1.73±0.76% and 0.46±0.39%, respectively, FIG. 2b). The vaccine-induced CD8$^+$ T cells had a much higher proliferative capacity compared to the CD4$^+$ T cell compartment. As with the CD4$^+$ T cell response the DNA group had the highest response with 41.3±9.2% of cells proliferating compared to 18.7±5.02% in the DNA+12 group and 17.9±5.33% in the DNA+RANTES group (FIG. 2c). Although the DNA group had a higher proliferative response, the difference was not statistically significant.

Figure 3A:
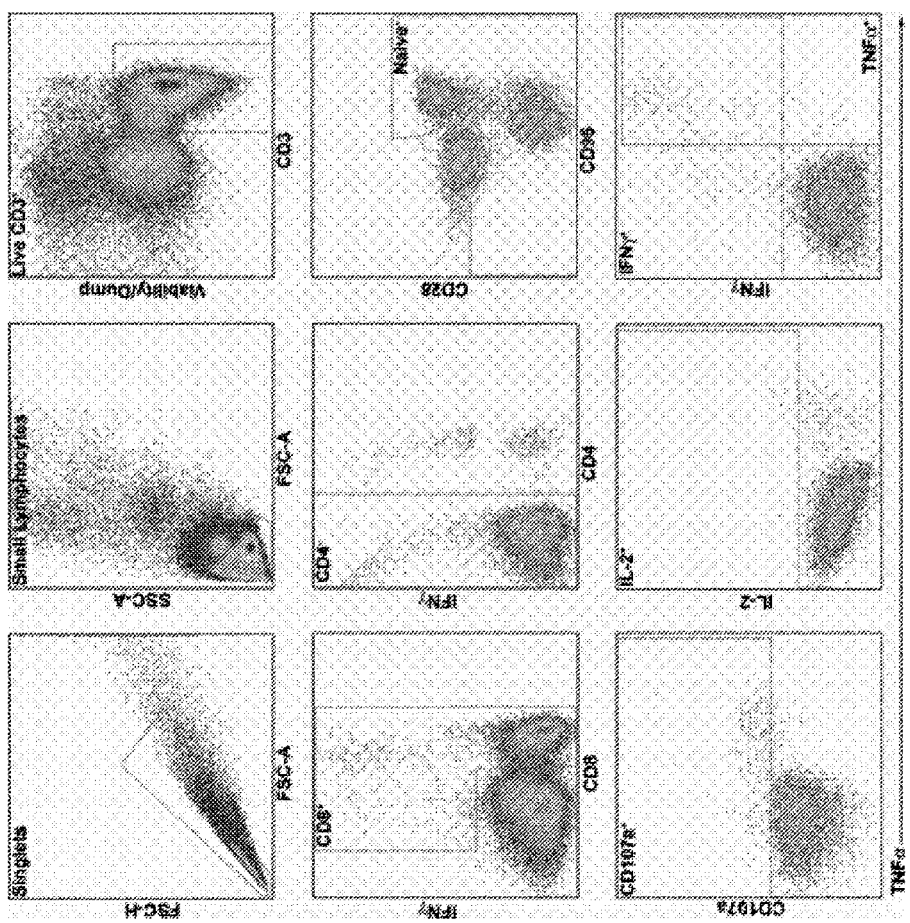
Figure 3B:
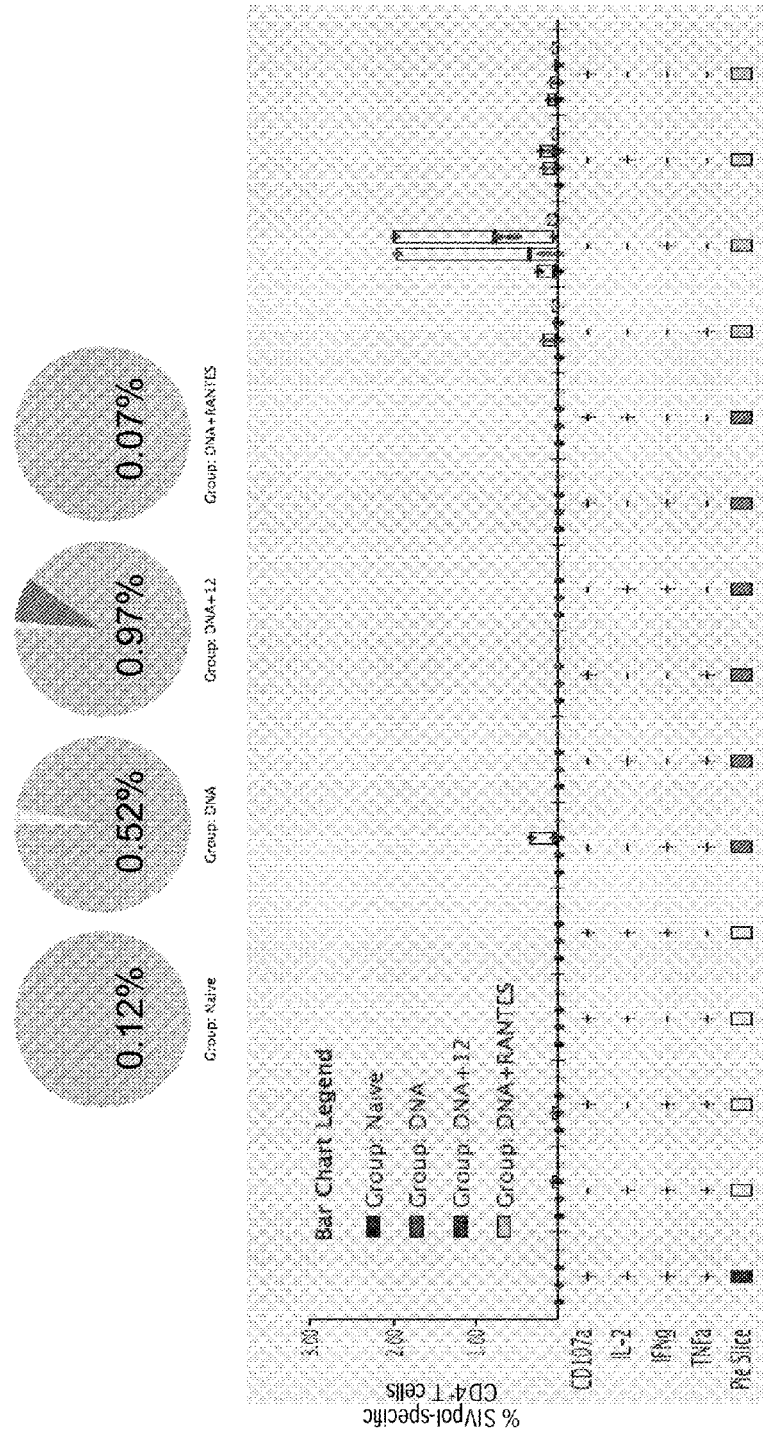

Co-Immunization of Plasmid rhIL-12 Enhances Cytokine Production by Antigen-Specific $CD4^+$ T Cells To determine the quality of the vaccine-induced response, SIVpol-specific $CD4^+$ T cells were assessed for the production of IFNγ, IL-2, TNFα, and CD107a (FIG. 3a). Using Boolean gating the ability of individual cells to produce multiple cytokines, i.e. polyfunctionality of the vaccine-induced $CD4^+$ T cell response. was assessed. Immunization with DNA alone resulted in an average SIVpol response of 0.52±0.29% (FIG. 3b). The addition of IL-12 to the immunization resulted in an almost two-fold increase in $CD4^+$ T functional response (0.97±0.26%). Interestingly, the addition of RANTES did not induce a response that was higher than the control group (0.07±0.03% and 0.12±0.12%, respectively). While majority of responses in all vaccination groups were monofunctional, the DNA+12 group had the largest proportion of cells capable of two or more functions, with the predominant dual function population being $IFNγ^+ TNFα^+$ producing cells.

Co-Immunization of Plasmid rhIL-12 Favors IFNγ Production by $CD8^+$ T Cells

Figure 3C:
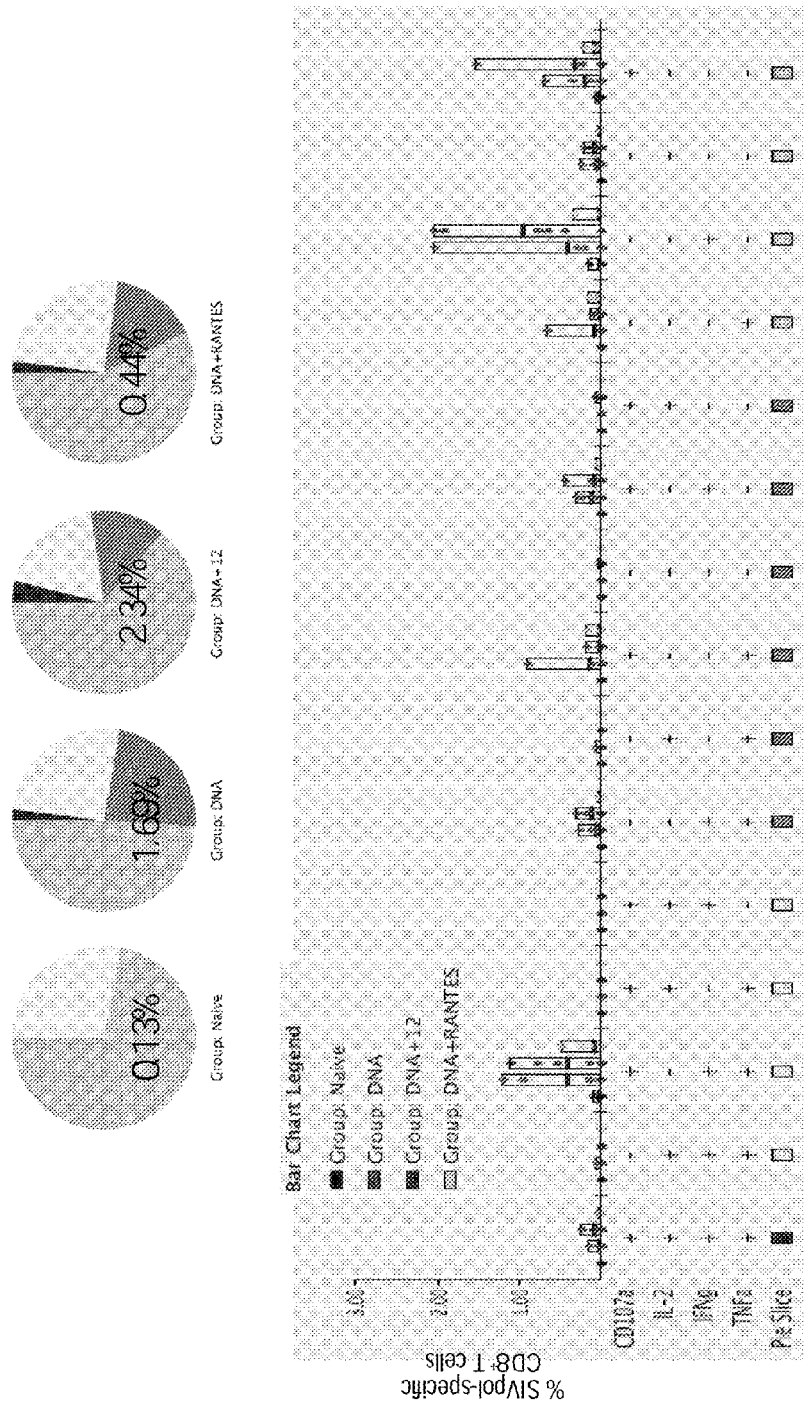

Having seen distinct phenotypic differences in the $CD4^+$ T cell compartment, the phenotype of the $CD8^+$ T cell compartment was evaluated next. Cytokine production by SIVpol-specific $CD8^+$ T cells was examined. The magnitude of the functional response reflected what was observed in the $CD4^+$ T cell compartment. The DNA+12 group had the highest response with 2.34±0.62% of $CD8^+$ T cells producing at least one function (FIG. 3c). The DNA group had a slightly lower response with 1.69±0.63% while the DNA+RANTES group had a four-fold lower response with 0.44±0.16% of $CD8^+$ T cells responding.

Figure 3D:
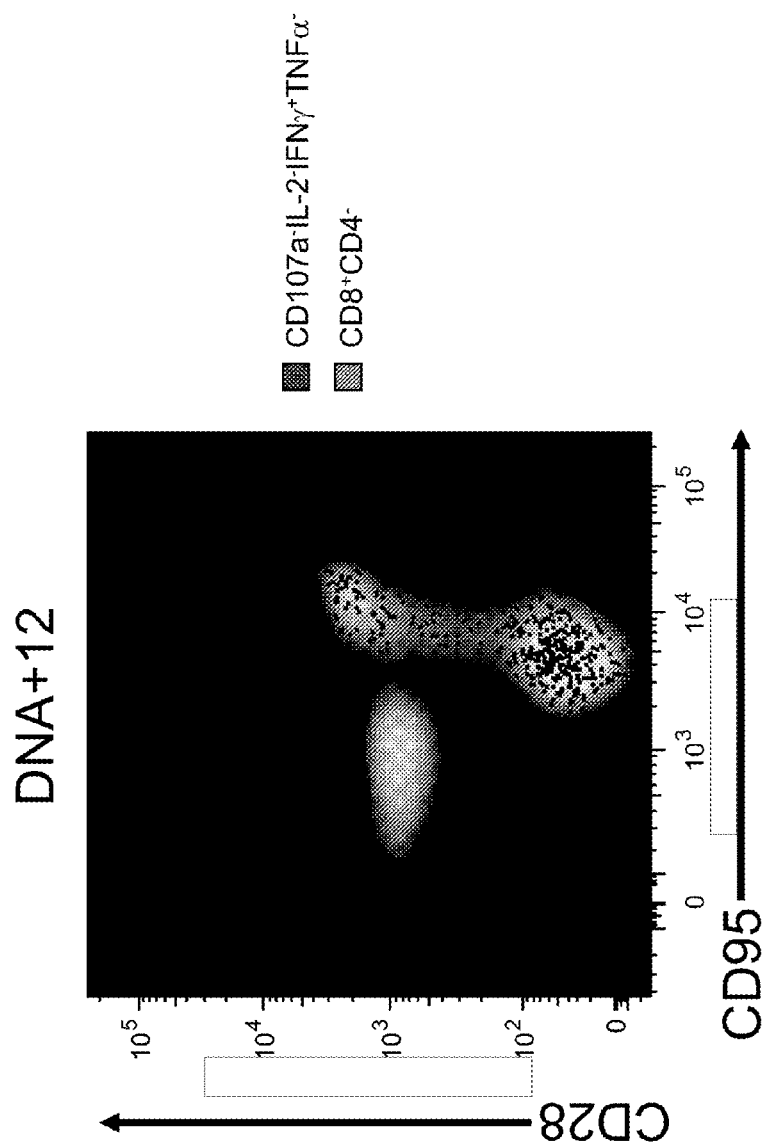

In addition to having the response with the highest magnitude, four out of the six animals in the DNA+12 group had a population of cells that were capable of all four functions compared to two animals in the DNA group and one animal in the DNA+RANTES group. Despite having a larger proportion of the response capable of all four functions, the predominant response in the DNA+12 group is the IFNγ monofunctional population. This could suggest that the addition of IL-12 as a molecular adjuvant induces a high frequency of terminally differentiated effector-like cells that have lost the ability to produce cytokines, except for IFNγ. However, the memory phenotype of these cells showed that they were distributed in both the effector memory and central memory T cell compartments, as defined by CD28 and CD95 staining (FIG. 3d), supporting the functional nature of these T cells.

Maintenance of the Vaccine-Induced Response

Figure 4A:
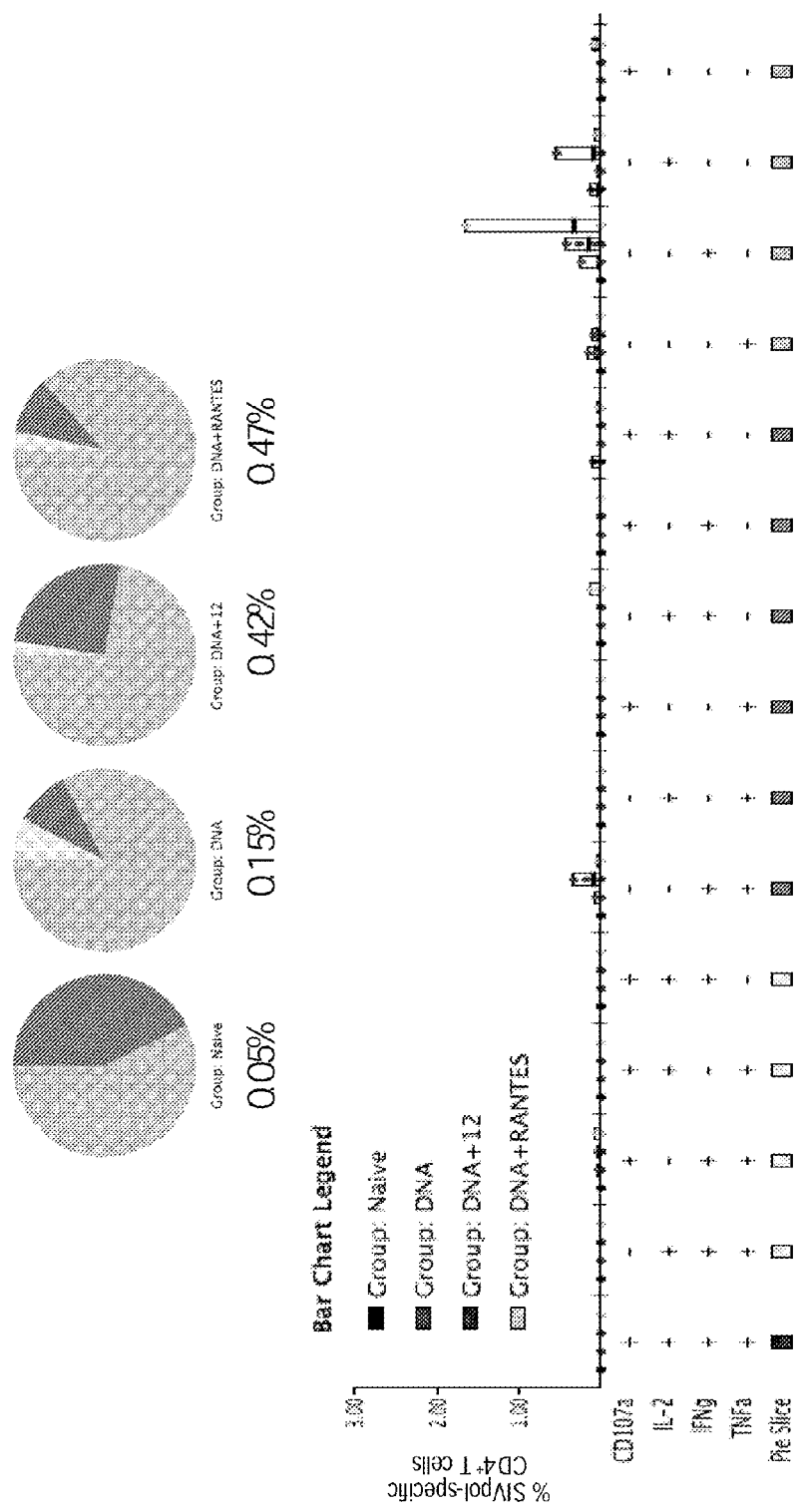

Having observed a dramatic induction of the cellular immune response by this plasmid vaccine delivered by EP, experiments were performed to determine if these populations could be maintained in the memory phase of the immune response. Animals were rested for eight months and cytokine production was examined in response to ex vivo SIVpol stimulation. In the $CD4^+$ T cell compartment, the DNA and DNA+12 group had SIVpol responses that contracted to levels that were half the magnitude, or less, of the post-immunization immune response (0.15±0.11% and 0.42±0.09%, respectively) (FIG. 4a). One exception was the RANTES group that had an average response of 0.47±037%. However, one animal in the group had an abnormally high IFNγ response that accounted for the large memory response. As observed following the fourth immunization the IFNγ monofunctional cells were the predominant population in all groups.

The same contraction of the immune response in the memory $CD8^+$ T cell compartment was observed (FIG. 4b). Although no four functional cells were detected, all three groups maintained a detectable $CD107a^+IFNγ^+TNFα^+$ response as well as the large $IFNγ^+$ monofunctional population that was observed after the fourth immunization. These data suggest that enhanced DNA vaccination with or without molecular adjuvants are capable of inducing long-lived, polyfunctional memory responses.

Figure 5D:
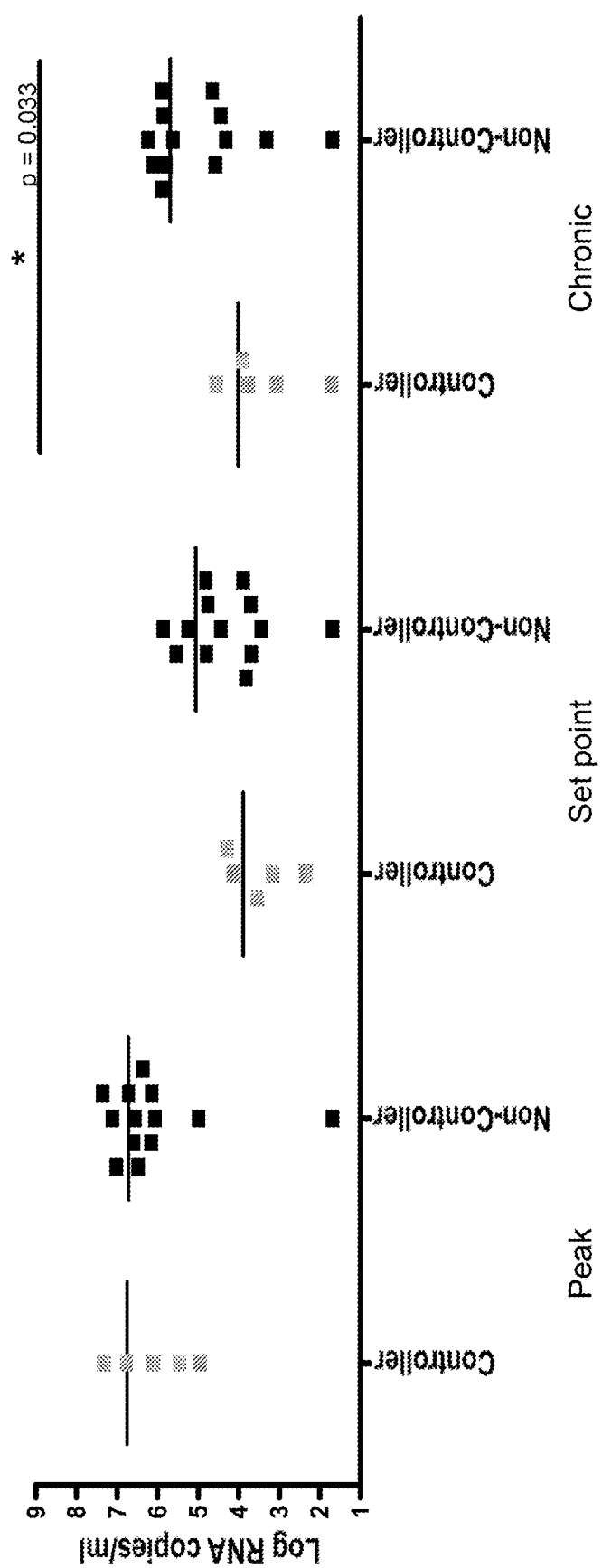
Figure 6A:
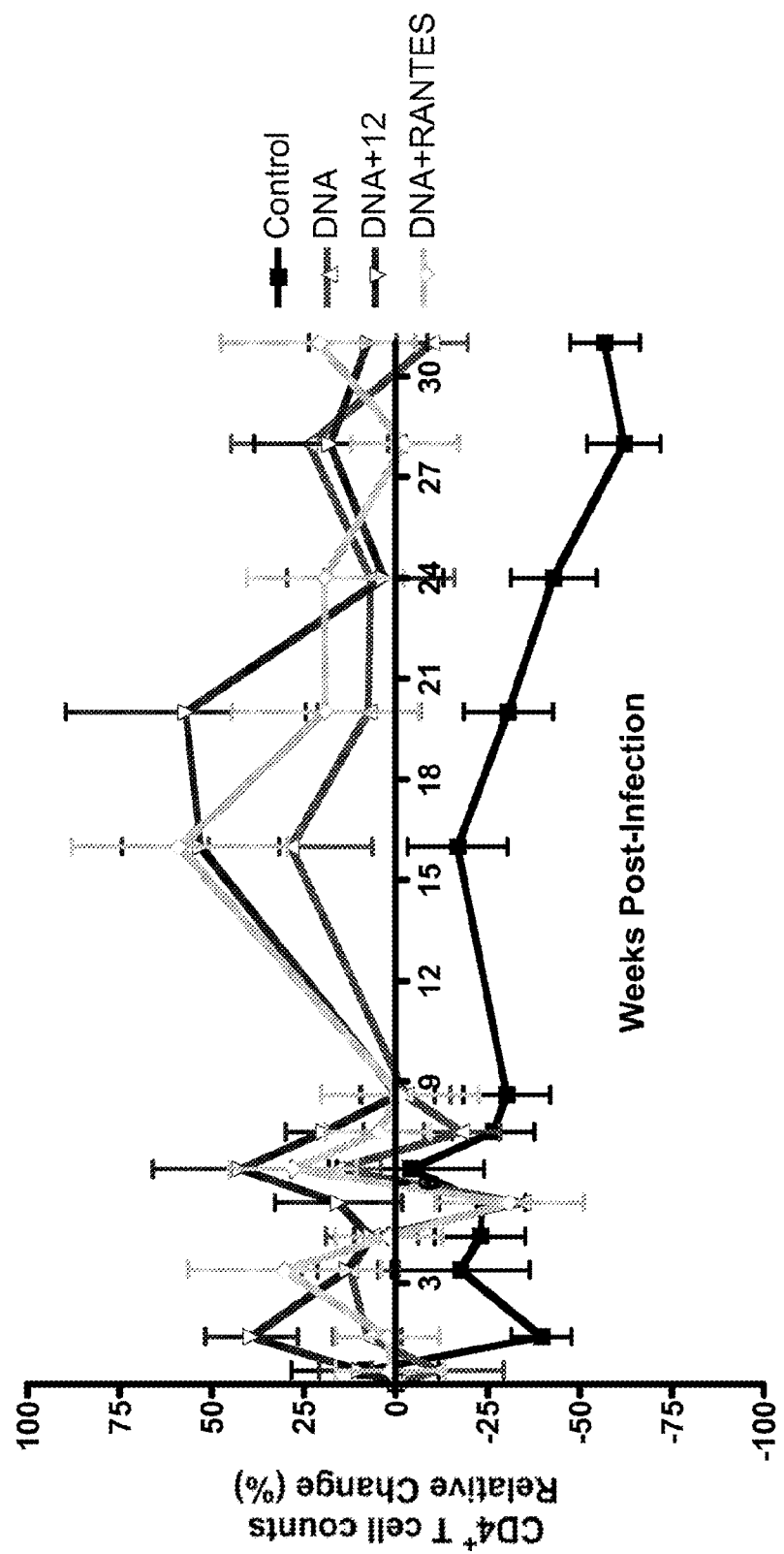
Figure 6B:
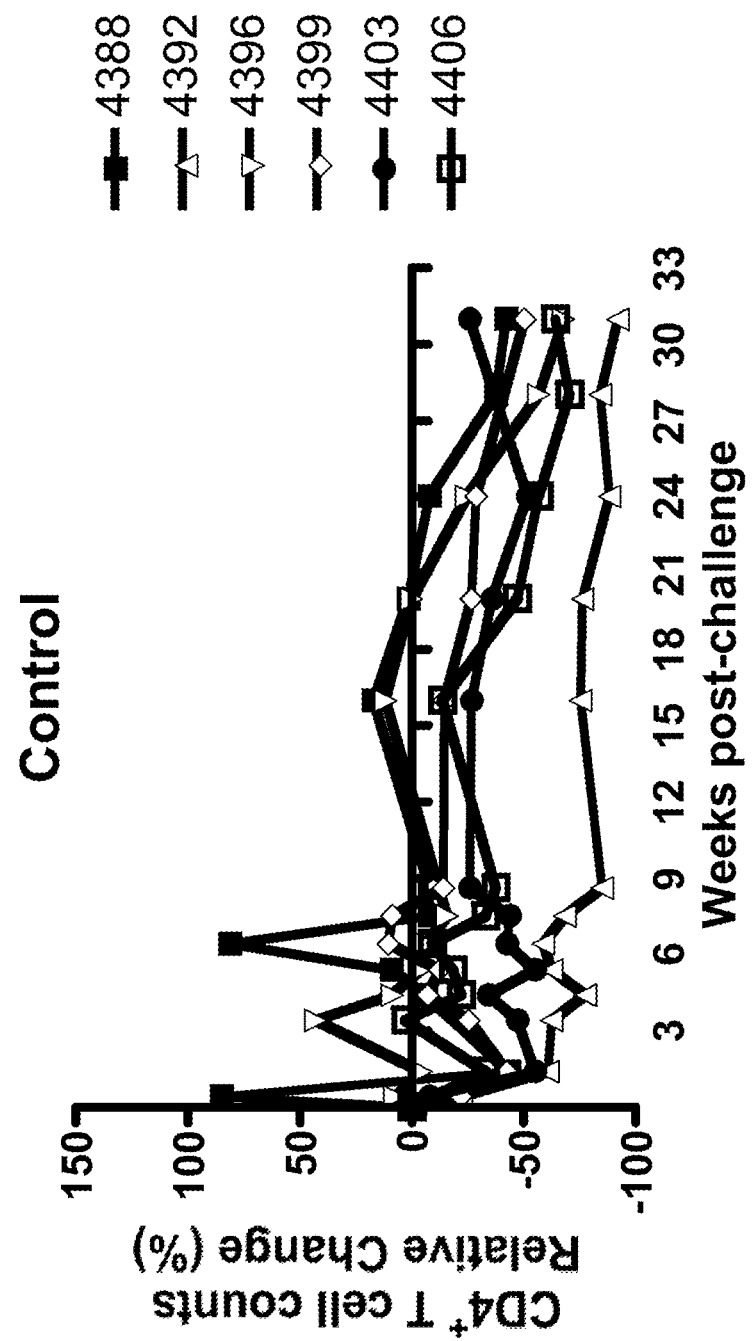
Figure 6D:
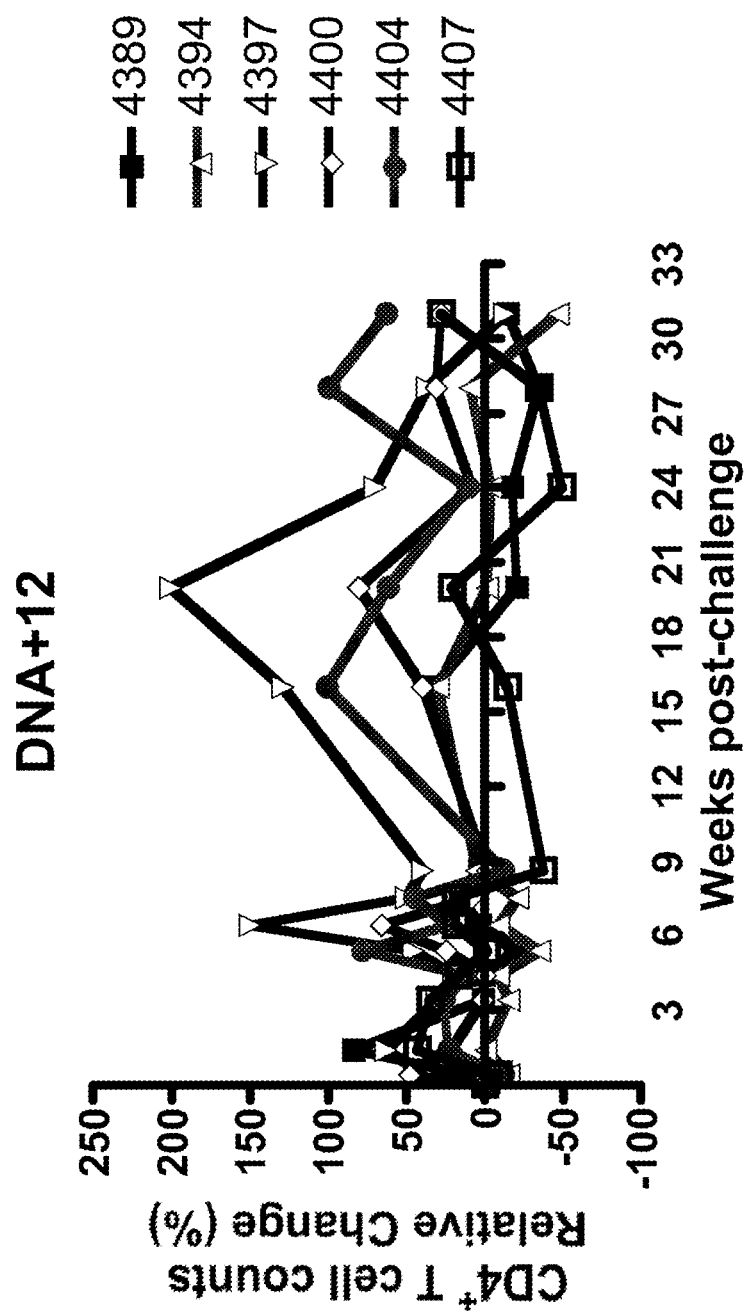

Co-Immunization with Plasmid IL-12 and RANTES Results in a Significant Decrease in Viral Loads at Set Point Next, experiments were undertaken to determine if these vaccine specific cellular responses, maintained 8 months after immunization, could impact viral loads following a SIV-mac251 mucosal challenge. The animals were challenged with 25 monkey infectious doses (MID) of SIVmac251 by the intrarectal route. Viral loads were assessed every week for two months and every month thereafter up to 9 months post-challenge. Taken cumulatively, the vaccinated animals as a whole (regardless of IL-12 or RANTES) demonstrated significantly lower peak viremia relative to non-vaccinated controls (p=0.027) and a lower viral set point (p=0.01) (FIG. 5a). Further examination of the average viral load for each group revealed the enhanced control of viral replication in the DNA+RANTES group over time (FIG. 5b). At the peak of viremia, the DNA and DNA+12 groups had a reduction of viral load (1.12 and 0.82 logs, respectively) compared to the Naïve group. The addition of RANTES to the immunization resulted in a significant 2.0 log decrease in peak viremia (p=0.016). At set point, the DNA group on average only exhibited a 0.62 log decrease in viral load compared to the Naïve group. The DNA+12 and the DNA+RANTES groups had significant 1.5 (p=0.029) and 2.2 (p=0.003) log decreases in set point viral loads compared to the Naïve group. However at the end of the study, only the DNA+RANTES group had a significant reduction in viral replication, as determined by area under the curve analysis (p=0.008) (FIG. 5c).

Previous SIV challenge studies have identified several MHC-I alleles that are associated with natural control of viral replication. To evaluate the potential contribution of host MHC-I genetics in this study, comprehensive sequence-based typing of all of the animals was performed retrospectively (Table 5). Post-hoc analysis revealed that there were four animals that expressed the protective Mamu-B*003 allele, two in the DNA+RANTES group and one each in the DNA and DNA+12 group. We also identified a Mamu-B*017 animal in the DNA+12 group. Another animal in the DNA+RANTES group was found to have a novel class I allele highly similar to Mamu-B*01702. Although significantly lower viral loads were observed in the animals with protective haplotypes at the end of the study (p=0.033) (FIG. 5d), there was no statistical difference in peak (p=0.968) and set point (p=0.161) viral loads. Thus, these protective alleles may have contributed to control of viral replication during chronic infection, but they do not appear to correlate with a vaccine effect on control of viral replication observed early after infection.

DNA Vaccination Prevents $CD4^+$ T Cell Loss Following SIVmac251 Mucosal Challenge Having observed reduced levels of viral replication at set point in the vaccinated groups, protection by another immune parameter was evaluated. To this end $CD4^+$ T cell counts were monitored every two weeks for 2 months and then every four weeks thereafter. The naïve group did undergo a sustained $CD4^+$ T cell loss over the nine months following challenge, resulting in a 50% loss compared to baseline counts (FIGS. 6a-6e). In contrast, the vaccinated groups did not show any sustained reduction in CD4+ T cell counts. Thus DNA vaccination with or without immune adjuvants protected animals from CD4+ T cell loss through nine months after infection with SIVmac251.

No Enhancement of CCR5 Expression on Antigen-Specific CD8+ T Cells in Peripheral Blood Following RANTES Co-Immunization.

Figure 7A:
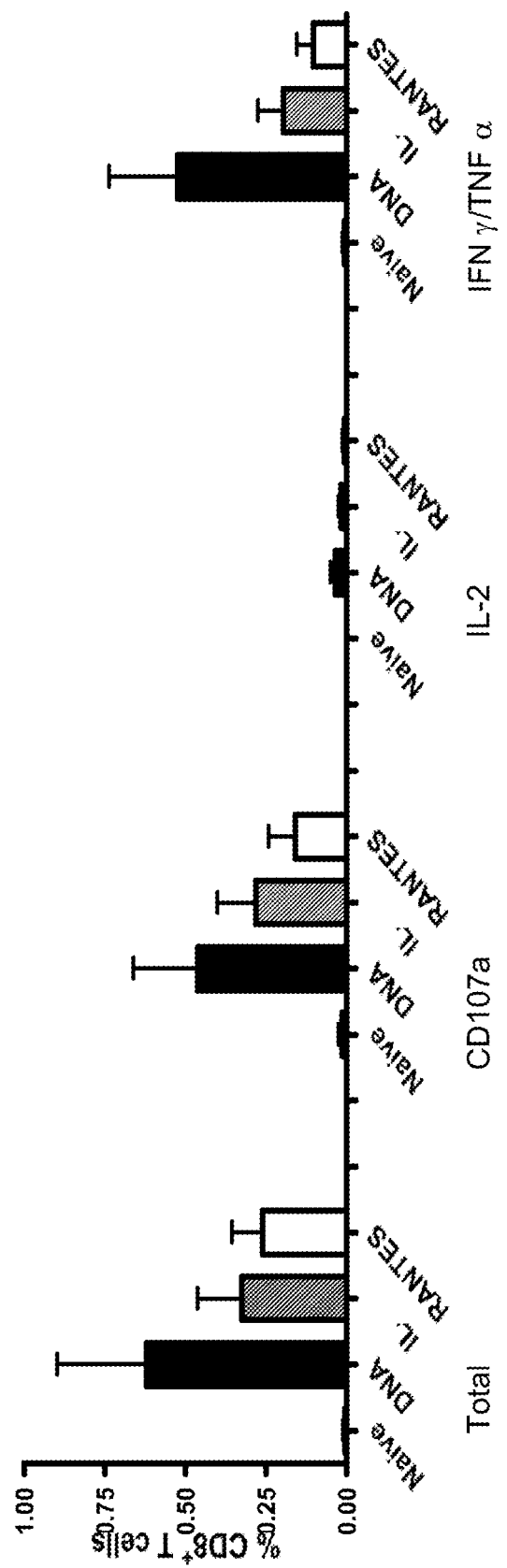
FIGS. 7a and 7b show the induction of CCR5$^+$ T cells following immunization. Cryo-preserved PBMCs isolated after the third immunization (i.e. the last immunization to include molecular adjuvants) were stimulated with SIVpol peptides and antigen-specific cells were identified by the production of IFNγ, TNFα, IL-2 or CD107a mobilization by ICS. The frequency of SIVpol-specific, CCR5$^+$ cells was determined for CD8$^+$ T cell compartments (data shown in FIG. 7a) and CD4$^+$ T cell compartments (data shown in FIG. 7b). The data are shown as frequencies in the total CD8 or CD4 populations. IFNγ and TNFα were combined on the same fluorophore to accommodate additional stains in this panel.
Figure 7B:
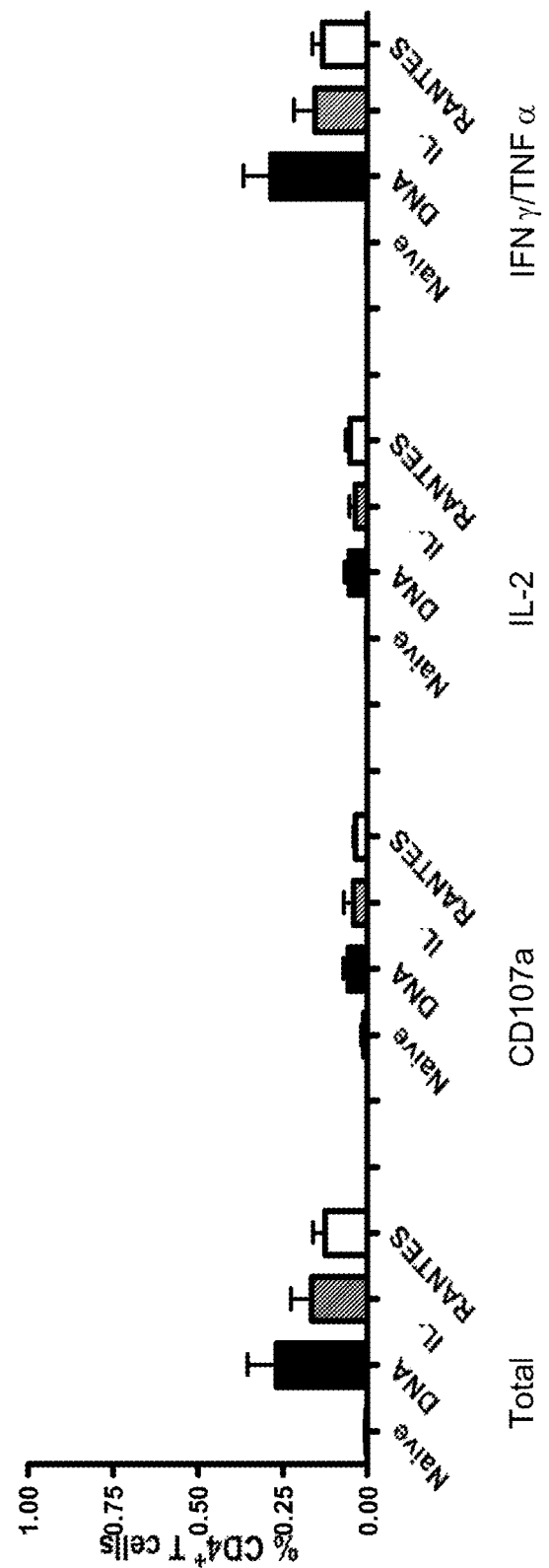

Experiments were performed to determine if co-immunization with RANTES might influence levels of antigen-specific CD8+ T cells that could be mobilized to the site of infection and impact viral replication following challenge. ICS was performed for CD107a, IL-2, IFNg and TNFa on cryo-preserved cells isolated following the third immunization. SIVpol-specific responses were first determined for each function and the expression of CCR5 on those cells was measured. A lower frequency of antigen-specific CD8+ T cells that expressed CCR5 was observed in the DNA+RANTES group in the periphery (0.26±0.09%) compared to the DNA and DNA+12 groups (0.62±0.28% and 0.33±0.14%, respectively) (FIG. 7a). However this difference was not statistically significant (Kruskal-Wallis, p=0.056). Similar trends were seen in the CD4+ T cell compartment, with the DNA group having the highest frequency (0.27±0.09%) of SIVpol-specific CCR5+ cells and DNA+RANTES having the lowest frequency (0.13±0.04%) in peripheral blood (FIG. 7b). This data supports that RANTES modulated either the levels of CCR5 expression on antigen specific T cells or alternatively mobilized these cells to other immune sites.

Discussion

The ability of EP and plasmid IL-12 to dramatically enhance the immunogenicity of a HIV plasmid antigen was have previously reported in a primate pilot study. RANTES was also observed to be a very effective adjuvant in mouse studies. The experiments described herein were designed to determine if these strategies could enhance the immunogenicity of a plasmid SIV vaccine and to characterize these responses in an attempt to identify any subpopulation of the cellular response that may contribute to the control of viral replication. Consensus SIV antigens were tested and examined to determine if the enhanced responses could impact an unmatched, mucosal SIVmac251 viral challenge.

In agreement with previous work, EP was able to dramatically enhance the vaccine-specific IFNγ response to very high levels. In contrast to earlier studies, the magnitude of the responses in this study was over three-fold higher, consistent with the addition of construct optimization strategies used in this study. However, no further enhancement in ELISpot counts was observed when plasmid IL-12 was used as an adjuvant, except early in the study. This may be due to the higher dose of DNA that was used or the concentration of the DNA; the vaccine was formulated at 10 mg/mL compared to 2 mg/mL in the pilot study. The use of highly optimized DNA constructs at higher doses and concentrations appear to overcome the difference in immunogenicity that is observed when the formulated vaccine is delivered at lower, more dilute doses. Such formulations may have important consequences for the DNA platform.

While impressive IFNγ ELISpot counts were observed, it is important that this parameter alone should not be the sole factor to determine the efficacy of a vaccine candidate as a number of studies have shown that ELISpot responses do not correlate directly with control of viral replication. To this end, a number of parameters that have been suggested to be desirable for an effective HIV vaccine were evaluated. First, results from the recent Merck STEP trial have suggested that the induction of a broad immune response will be important for a successful vaccine. On average, subjects vaccinated with Merck's recombinant Ad5 vector had a breadth of response that was limited to three to five epitopes. In evaluating the responses to the SIVpol antigen by matrix peptide mapping, unprecedented positive responses were observed for the majority of peptide pools indicating broad epitope coverage in all of the immunization groups. It is also interesting that the DNA+RANTES vaccine, which induced the most diverse epitope responses, had the best control of viral replication.

Studies in long-term non-progressors have shown that the non-progressors have more polyfunctional CD8+ T cells than progressors, suggesting that these polyfunctional populations may be important in the control of virus. The induction of polyfunctional responses were observed in both the DNA and DNA+12 groups for both CD4+ and CD8+ T cell compartments. However there were a few interesting observations. First, in the CD4+ T cell compartment the response rate and the magnitude of responses to SIVpol in the DNA group were lower than that of the DNA+12 group. Second, in both the CD4+ and CD8+ T cell compartment, the DNA+12 group had a high proportion of their response consisting of IFNγ monofunctional cells. In models of T cell memory differentiation, such IFNγ monofunctional cells are thought to represent terminal effectors. To address this possibility the memory phenotype of these monofunctional cells were examined by CD28 and CD95 staining. In this instance these responses were found to be comprised of cells from both the CD28+ CD95+ central memory population as well as the CD28− CD95+ effector population. It is possible that the CD28+ CD95+ cells are not actually monofunctional but also possess some other function that was not assessed in our polyfunctional panel. This hypothesis warrants attention in future studies.

A number of DNA prime/viral vector boost studies have shown some efficacy in viral load reduction in the SHIV89.6P challenge model. However the utility of this model in predicting vaccine efficacy has been debated. Thus the efficacy of the DNA vaccine induced immune response in a more stringent, high-dose SIVmac251 mucosal challenge model was evaluated. Other studies using this challenge model have reported modest effects on viral replication.

There was a dramatic difference in protection of CD4 T cell loss observed between all the vaccinated animals and the control animals. Vaccinated animals were protected from CD4 T cell loss regardless of adjuvant for the entire course of the study. Furthermore, differences between the vaccination groups were seen in the control of viral replication following challenge. While both the DNA and DNA+12 groups exhibited approximately 1 log reductions in peak viremia relative to the unvaccinated controls, the DNA+RANTES group exhibited a significant 2.2 log reduction of peak viral loads compared to the Naive group. While the DNA group did not have a significant reduction of viral load at set point, the groups adjuvanted with IL-12 and RANTES had significantly lower viral loads. At week 35, only the DNA+RANTES group exhibited a sustained, significant impact on viral loads compared to the Naive controls.

Numerous studies in humans and macaques have demonstrated that certain MHC haplotypes are associated with natural control of virus. While most previous studies have examined MHC-I/disease association in Indian-origin rhesus macaques, the increasing use of Chinese-origin rhesus macaques for SIV vaccine studies has bolstered the need for similar studies in this understudied population to complement those done to date. To address this issue, comprehensive class I genotyping of all of the animals was performed after the challenge study had commenced. Post-hoc analysis revealed four animals that expressed the Manu-B*003 allele which is associated with strong protection against SIV replication; two in the DNA+RANTES group and one each in the DNA and DNA+12 group. A Mamu-B*017 animal was also identified in the DNA+12 group. Interestingly, a potentially protective Mamu-B*017-like novel allele was detected in a DNA+RANTES animal that never exhibited detectable plasma viral RNA after challenge. Significantly lower viral loads were observed in the animals with theses protective alleles at the end of the study (p=0.035), consistent with the importance of such class I alleles. In contrast however, there was no statistical difference in peak (p=0.561) and set point (p=0.056) viral loads of the protective haplotype animals. Thus the protective haplotypes were associated with control of virus during chronic infection but a vaccine effect was also observed in the control of viral replication early in infection. In addition, the lack of CD4$^+$ T cell depletion following challenge in the vaccination groups did not differ significantly between the animals with the Mamu-B*003 or Mamu-B*017 alleles versus the rest of the vaccinated animals. Taken together these data further indicate that DNA vaccination can contribute to protection in a SIVmac251 mucosal challenge.

The mechanism for enhanced viral suppression observed in the DNA+RANTES group is not known. It is clear from our assays that it is not due to the magnitude of the IFNγ response. One hypothesis is that the presence of RANTES during immunization would modulate the frequency of CCR5$^+$CD8$^+$ T cells. These cells would then home to site of infection, as has been reported for CCR5$^+$CD4$^+$ T cells, and be able to target infected CDe T cells and provide an improved outcome. To address this hypothesis in a preliminary fashion the frequency of antigen-specific CD8$^+$ T cells that expressed CCR5 was measured in the peripheral blood following immunization. Lower frequencies of these cells were observed in the DNA+RANTES group in the peripheral blood. This result, along with the lower frequencies of antigen-specific cells observed in the other assays, may reflect differential homing patterns (e.g. mucosal compartments) of the RANTES adjuvanted response compared to the other vaccination groups. In any event it is clear that RANTES modulated aspects of the immunobiology of the induced T cells and this modulation appears to benefit the host in the context of viral challenge. Future studies will need to be performed to further explore this important area.

Although a number of immune parameters were examined, no single assay was able to predict the outcome of viral challenge. The control of viral replication that was observed in this study was not associated with the development of neutralizing antibodies as none were detected following immunization. Recent studies have suggested that other cellular functions, such as cytotoxicity may be better indicators of protective immune responses. However perform in the vaccine induced immune response was not assessed due to the lack of a rhesus specific antibody. Based on the challenge outcome it appears clear that IFNγ ELISpot responses, while important, are segregating separately from other functions that could be better indicators of virus control. Further studies of the immune phenotype of the IL-12 and RANTES induced response will be important in determining a cellular mechanism for the decreased viral replication observed in this study.

The recent results of the Merck STEP trial has highlighted a number of issues which future T cell-based vaccine candidates will need to address, including: concerns of pre-existing vaccine vector serology, a requirement for significant improvement in the magnitude and breadth of the immune response over the Ad5 platform, and improved viral control in heterologous SIV mucosal challenge models. In this regard the collective data presented herein support that the combined DNA vaccine approaches described here are capable of inducing robust immune responses that are relevant to SIV infection while circumventing issues due to pre-existing serology. It may be of interest to combine these vaccines with vector approaches to partially bypass such serology based issues. Additionally, the magnitude of these responses and the ability to modulate the direction and phenotype of the induced immune response using molecular adjuvants may be a particularly useful tool for the study of vaccine relevant correlates in the SIV model.

TABLE 3

Immunization Schedule

| Immunization | DNA (n = 6) | DNA + 12 (n = 6) | DNA + RANTES (n = 6) | Naive (n = 6) |
|---|---|---|---|---|
| Week 0 | SIVgag SIVenv SIVpol | SIVgag SIVenv + IL-12 SIVpol | SIVgag SIVenv + RANTES SIVpol | Control |
| Week 8 | SIVgag SIVenv SIVpol | SIVgag SIVenv + IL-12 SIVpol | SIVgag SIVenv + RANTES SIVpol | Control |
| Week 12 | SIVgag SIVenv SIVpol | SIVgag SIVenv + IL-12 SIVpol | SIVgag SIVenv + RANTES SIVpol | Control |
| Week 24 | SIVgag SIVenv SIVpol | SIVgag SIVenv SIVpol | SIVgag SIVenv SIVpol | Control |

TABLE 4

SIVpol Epitope Mapping

| Group | Minimum | Maximum |
|---|---|---|
| DNA | 56.33 ± 14.76 | 171 ± 43.11 |
| DNA + 12 | 43.67 ± 12.47 | 128 ± 37.58 |
| DNA + RANTES | 68 ± 3.67 | 188 ± 14.12 |

Maximum number represents total number of positive peptides. Minimum number calculated by dividing positive peptide runs, 2 or more neighboring peptides, by 3 and rounding up to the nearest integer. Group average ± S.E.M are shown for minimum and maximum epitope estimates.

TABLE 5

MHC-I Genotyping

| Sanger or 454 Typing | MHC Haplotype Associated with SIV Control | Animal ID | Sequences Evaluated | Unique MHC-I Alleles | B*00301 | B*00301/02 | B*01701/02 | B-017nov |
|---|---|---|---|---|---|---|---|---|
| S | N | 4403 | 92 | 12 | | | | |
| S | N | 4396 | 65 | 9 | | | | |
| S | N | 4406 | 148 | 9 | | | | |

TABLE 5-continued

MHC-I Genotyping

| Sanger or 454 Typing | MHC Haplotype Associated with SIV Control | Animal ID | Sequences Evaluated | Unique MHC-I Alleles | B*00301 | B*00301/02 | B*01701/02 | B-017nov |
|---|---|---|---|---|---|---|---|---|
| S | N | 4388 | 71 | 8 | | | | |
| S | N | 4399 | 73 | 10 | | | | |
| S | N | 4392 | 107 | 10 | | | | |
| S | Y | 4413 | 38 | 4 | | 34.2 | | |
| S | N | 4421 | 110 | 6 | | | | |
| 454 | N | 4416 | 1083 | 17 | | | | |
| S | N | 4411 | 117 | 12 | | | | |
| S | N | 4387 | 44 | 7 | | | | |
| S | N | 4425 | 147 | 6 | | | | |
| 454 | Y | 4404 | 7508 | 14 | | 15.5 | | |
| 454 | Y | 4394 | 7368 | 22 | | | 8.6 | |
| S | N | 4400 | 151 | 13 | | | | |
| S | N | 4397 | 136 | 12 | | | | |
| S | N | 4389 | 158 | 19 | | | | |
| 454 | N | 4407 | 8229 | 18 | | | | |
| 454 | ? | 4424 | 750 | 21 | | | | 12.1 |
| S | Y | 4408 | 100 | 12 | | 31.0 | | |
| S | Y | 4420 | 141 | 9 | 28.4 | | | |
| S | N | 4417 | 58 | 6 | | | | |
| S | N | 4415 | 96 | 11 | | | | |
| S | N | 4410 | 126 | 11 | | | | |

Comprehensive MHC class I genotypes of Chinese-origin rhesus macaques determined by Sanger-based and Roche/454 pyrosequence-based typing. MHC class I sequences from each animal were compared to an in-house database of all known Mamu sequences using BLASTN. Pyrosequencing provided significantly greater depth of coverage, but increased ambiguity between highly similar alleles due to the short templates evaluated. The percentage of sequence reads corresponding to a given allele in each animal are >5.0% (burgundy). Animals observed with MHC-I alleles or haplotypes associated with control of SIV replication (Mamu-B*003 and Mamu-B*017) are indicated in green. One animal (#4424) expressed a novel Mamu-B allele highly similar to Mamu-B*017, which may also be associated with SIV control. Other alleles associated with control, such as the Indian origin rhesus macaque alleles Mamu-A*001, Mamu-B*008 or Mamu-B*047, were not observed in this cohort of Chinese-origin rhesus macaques.

Example 2

Synthesis and Cloning of Human RANTES (pCCL5 ECRO–ECRU=IgE, Codon/RNA Optimized)

The 348 bp gene for optimized human CCL5 (pHuCCL5ECRO) was designed, synthesized and cloned in the following manner. Codon usage was adapted to the codon bias of human genes resulting in a high CAI value (non optimized: 0.81; optimized: 0.97). For design and synthesis, codons were selected so that regions of very high (>80%) or very low (<30%) GC content were avoided where possible. In this regard, it has been determined that the wildtype human CCL5 gene uses rare codons with a high frequency and the GC content was average (57%) which may facilitate a small level of rapid mRNA turnover. Therefore, GC-content was increased slightly (62%) to improve mRNA half-life. During the optimization process, the following cis-acting sequence motifs were avoided: internal TATA-boxes, chi-sites and ribosomal entry sites, AT-rich or GC-rich sequence stretches, ARE, INS, CRS sequence elements, repeat sequences and RNA secondary structures, (cryptic) splice donor and acceptor sites and branch points. Following analysis, only 1 negatively cis-acting motif was identified and removed. Gene synthesis of the optimized human CCL5 was carried out by Geneart, Inc. (Germany). The synthetic highly codon/RNA optimized human CCL5 gene was assembled from synthetic oligonucleotides. A Kozak sequence (GCCACC) was introduced to increase translational initiation, an IgE leader sequence was introduced, and two stop codons were added to ensure efficient termination. The fragment was cloned into pVAXI using EcoRI and XhoI restriction sites. The plasmid DNA was purified by VGX pharmaceuticals (Pure Yield™ Plasmid Midiprep, Promega) from transformed bacteria and concentration determined by UV spectroscopy. The final DNA sequence of human CCL5 (phumCCL5ECRO) was verified by sequencing and found to be 100% congruence.

Example 3

The attached sequence listing contains SEQ ID NOs:1-8. SEQ ID NO:1 is the codon/RNA optimized nucleic acid sequence that encodes human RANTES. SEQ ID NO:2 is the amino acid sequence of human RANTES encoded by SEQ ID NO:1. SEQ ID NO:3 is the codon/RNA optimized nucleic acid sequence that encodes a RANTES protein having an IgE leader sequences linked at the N-terminal of human RANTES. SEQ ID NO:4 is the a RANTES protein having an IgE leader sequences linked at the N-terminal of human RANTES that is encoded by SEQ ID NO:3. SEQ ID NO:5 comprises the same the codon/RNA optimized nucleic acid sequence that encodes a RANTES protein having an IgE leader sequences linked at the N-terminal of human RANTES as disclosed in SEQ ID NO:3 but with an additional Kozak sequence in the 5' untranslated region of the construct. SEQ ID NO:6, which is the same sequence as SEQ ID NO:4, is a RANTES protein having an IgE leader sequences linked at the N-terminal of human RANTES that is encoded by SEQ ID NO:3. SEQ ID NO:7 comprises the same the codon/RNA optimized nucleic acid sequence that encodes a RANTES protein having an IgE leader sequences linked at the N-terminal of human RANTES as disclosed in SEQ ID NO:3 and SEQ ID NO:5 but with an additional Kozak sequence in the 5' untranslated region of the construct of SEQ ID NO:5 and restriction enzyme sites at the 5' and 3' ends which are useful procedures involving the insertion and cloning of the construct in a plasmid. SEQ ID NO:8, which is the same sequence as SEQ ID NO:4 and SEQ ID NO:6, is a RANTES protein having an IgE leader sequences linked at the N-terminal of human RANTES that is encoded by SEQ ID NO:3 and SEQ ID NO:5.

The invention claimed is:

1. An isolated nucleic acid molecule comprising a nucleotide sequence selected from the group consisting of: SEQ ID NO:1 and a nucleic acid sequence that is 95% homologous to SEQ ID NO:1.

2. The isolated nucleic acid molecule of claim 1 comprising SEQ ID NO:1.

3. The isolated nucleic acid molecule of claim 1 comprising a nucleic acid sequence that comprises an IgE leader coding sequence linked to SEQ ID NO:1 at the 5' end of the coding sequence.

4. The isolated nucleic acid molecule of claim 3, wherein the nucleic acid sequence that comprises an IgE leader coding sequence linked to SEQ ID NO:1 at the 5' end of the coding sequence comprises SEQ ID NO:3.

5. The isolated nucleic acid molecule of claim 3 that further comprises a Kozak sequence in the 5' untranslated region.

6. The isolated nucleic acid molecule of claim 5, wherein the nucleic acid sequence that comprises an IgE leader coding sequence linked to SEQ ID NO:1 at the 5' end of the coding sequence and a Kozak sequence in the 5' untranslated region comprises SEQ ID NO:5.

7. The isolated nucleic acid molecule of claim 1 wherein said nucleic acid sequence is operably linked to regulatory elements that are functional in a human cell.

8. The isolated nucleic acid molecule of claim 7 wherein said isolated nucleic acid molecule is a plasmid.

9. A method of inducing an immune response against one or more of a human immunodeficiency virus (HIV) antigen and a simian immunodeficiency virus (SIV) antigen comprising the step of administering to an individual a nucleic acid molecule of claim 1.

10. A recombinant viral vector comprising a nucleic acid molecule of claim 1.

11. The recombinant viral vector of claim 10 further comprising a nucleic acid sequence that encodes an immunogen operably linked to regulatory elements.

12. The recombinant viral vector of claim 10 wherein said immunogen is a pathogen antigen, a cancer-associated antigen or an antigen associated with cells involved in autoimmune diseases.

13. The recombinant viral vector of claim 12 wherein said immunogen is a pathogen antigen.

14. A live attenuated pathogen comprising a nucleic acid molecule of claim 1.

15. A method of reducing human immunodeficiency virus (HIV) viral replication comprising the step of administering to an individual a nucleic acid molecule of claim 1.

16. A composition comprising a) a plurality of one or more nucleic acid molecules comprising one or more nucleic acid sequences selected from the group consisting of: SEQ ID NO:1 and a nucleic acid sequence that is 95% homologous to SEQ ID NO:1, and b) one or more additional nucleic acid sequences that encode one or more immunogens.

17. The composition of claim 16 comprising a plurality of one or more nucleic acid molecules that comprise said one or more additional nucleic acid sequences that encode one or more immunogens, wherein said plurality of one or more nucleic acid molecules that comprise said one or more additional nucleic acid sequences that encode one or more immunogens are different from the plurality of nucleic acid molecules set forth in a).

18. The composition of claim 16 wherein the plurality of nucleic acid molecules set forth in a) comprises SEQ ID NO:1.

19. The composition of claim 16 wherein the plurality of nucleic acid molecules set forth in a) comprise a nucleic acid sequence that comprises an IgE leader coding sequence linked to SEQ ID NO:1 at the 5' end of the coding sequence.

20. The composition of claim 19 wherein the nucleic acid sequence that comprises an IgE leader coding sequence linked to SEQ ID NO:1 at the 5' end of the coding sequence comprises SEQ ID NO:3.

21. The composition of claim 19 wherein the plurality of nucleic acid molecules that comprise an IgE leader coding sequence linked to SEQ ID NO:1 at the 5' end of the coding sequence and further comprise a Kozak sequence in the 5' untranslated region.

22. The composition of claim 21 wherein the plurality of nucleic acid molecules that comprise an IgE leader coding sequence linked to SEQ ID NO:1 at the 5' end of the coding sequence and a Kozak sequence in the 5' untranslated region comprise SEQ ID NO:5.

23. The composition of claim 16 wherein the nucleic acid sequences set forth in a) and b) are each operably linked to regulatory elements that are functional in a human cell.

24. The composition of claim 16 wherein the nucleic acid sequences set forth in a) and b) are comprised in one or more expression vectors.

25. The composition of claim 24 wherein the one or more expression vectors are plasmids.

26. The composition of claim 16 wherein said immunogen is a pathogen antigen, a cancer-associated antigen or an antigen associated with cells involved in autoimmune diseases.

27. The composition of claim 26 wherein said immunogen is a pathogen antigen.

28. The composition of claim 16 wherein said immunogen is an HIV (human immunodeficiency virus) antigen.

29. A method of inducing an immune response against a human immunodeficiency virus (HIV) antigen comprising the step of administering to an individual a composition of claim 28.

30. A method of reducing human immunodeficiency virus (HIV) viral replication comprising the step of administering to an individual a composition of claim 28.

* * * * *

SEQUENCE LISTING

<160> NUMBER OF SEQ ID NOS: 8

<210> SEQ ID NO 1
<211> LENGTH: 276
<212> TYPE: DNA
<213> ORGANISM: Homo sapiens

<400> SEQUENCE: 1
aaggtgtccg ccgccgccct ggccgtgatc ctgatcgcca ccgccctgtg tgccctgcc      60 agcgccagcc cctacagcag cgacaccacc ccctgctgct cgcctacat cgccagaccc     120 ctgcccagag cccacatcaa ggagtacttc tacaccagcg gcaagtgtag caatcccgcc    180
gtggtgttcg tgacccggaa gaacagacaa gtgtgcgcca ccccgagaa gaagtgggtg     240 agggagtaca tcaacagcct ggagatgagc tgatga                              276

<210> SEQ ID NO 2
<211> LENGTH: 90
<212> TYPE: PRT
<213> ORGANISM: Homo sapiens

<400> SEQUENCE: 2

Lys Val Ser Ala Ala Ala Leu Ala Val Ile Leu Ile Ala Thr Ala Leu
1               5                   10                  15

Cys Ala Pro Ala Ser Ala Ser Pro Tyr Ser Ser Asp Thr Thr Pro Cys
                20                  25                  30

Cys Phe Ala Tyr Ile Ala Arg Pro Leu Pro Arg Ala His Ile Lys Glu
            35                  40                  45

Tyr Phe Tyr Thr Ser Gly Lys Cys Ser Asn Pro Ala Val Val Phe Val
        50                  55                  60

Thr Arg Lys Asn Arg Gln Val Cys Ala Asn Pro Glu Lys Lys Trp Val
65                  70                  75                  80

Arg Glu Tyr Ile Asn Ser Leu Glu Met Ser
                85                  90

<210> SEQ ID NO 3
<211> LENGTH: 330
<212> TYPE: DNA
<213> ORGANISM: Artificial Sequence
<220> FEATURE:
<223> OTHER INFORMATION: RANTES and IgE nucleic acid

<400> SEQUENCE: 3
atggactgga cctggatcct gttcctggtg gccgctgcca caagagtgca cagcaaggtg      60
tccgccgccg ccctggccgt gatcctgatc gccaccgccc tgtgtgcccc tgccagcgcc    120
agcccctaca gcagcgacac caccccctgc tgcttcgcct acatcgccag accctgcc     180 agagcccaca tcaaggagta cttctacacc agcggcaagt gtagcaatcc cgccgtggtg   240
ttcgtgaccc ggaagaacag acaagtgtgc gccaaccccg agaagaagtg ggtgagggag   300
tacatcaaca gcctggagat gagctgatga                                     330

<210> SEQ ID NO 4
<211> LENGTH: 108
<212> TYPE: PRT
<213> ORGANISM: Artificial Sequence
<220> FEATURE:
<223> OTHER INFORMATION: RANTES + IgE amino acid

<400> SEQUENCE: 4

Met Asp Trp Thr Trp Ile Leu Phe Leu Val Ala Ala Ala Thr Arg Val

```
                1               5                  10                  15
His Ser Lys Val Ser Ala Ala Ala Leu Ala Val Ile Leu Ile Ala Thr
                    20                  25                  30

Ala Leu Cys Ala Pro Ala Ser Ala Ser Pro Tyr Ser Ser Asp Thr Thr
                35                  40                  45

Pro Cys Cys Phe Ala Tyr Ile Ala Arg Pro Leu Pro Arg Ala His Ile
            50                  55                  60

Lys Glu Tyr Phe Tyr Thr Ser Gly Lys Cys Ser Asn Pro Ala Val Val
65                  70                  75                  80

Phe Val Thr Arg Lys Asn Arg Gln Val Cys Ala Asn Pro Glu Lys Lys
                    85                  90                  95

Trp Val Arg Glu Tyr Ile Asn Ser Leu Glu Met Ser
                100                 105
```

<210> SEQ ID NO 5
<211> LENGTH: 336
<212> TYPE: DNA
<213> ORGANISM: Artificial Sequence
<220> FEATURE:
<223> OTHER INFORMATION: RANTES + IgE+ Kozak nucleic acid sequence

<400> SEQUENCE: 5

```
gccaccatgg actggacctg gatcctgttc ctggtggccg ctgccacaag agtgcacagc      60
aaggtgtccg ccgccgccct ggccgtgatc ctgatcgcca ccgccctgtg tgccccctgcc    120
agcgccagcc cctacagcag cgacaccacc ccctgctgct tcgcctacat cgccagaccc    180
ctgcccagag cccacatcaa ggagtacttc tacaccagcg gcaagtgtag caatcccgcc    240
gtggtgttcg tgacccggaa gaacagacaa gtgtgcgcca accccgagaa gaagtgggtg    300
agggagtaca tcaacagcct ggagatgagc tgatga                              336
```

<210> SEQ ID NO 6
<211> LENGTH: 108
<212> TYPE: PRT
<213> ORGANISM: Artificial Sequence
<220> FEATURE:
<223> OTHER INFORMATION: RANTES + IgE+ Kozak amino acid sequence

<400> SEQUENCE: 6

```
Met Asp Trp Thr Trp Ile Leu Phe Leu Val Ala Ala Thr Arg Val
1               5                   10                  15

His Ser Lys Val Ser Ala Ala Ala Leu Ala Val Ile Leu Ile Ala Thr
                    20                  25                  30

Ala Leu Cys Ala Pro Ala Ser Ala Ser Pro Tyr Ser Ser Asp Thr Thr
                35                  40                  45

Pro Cys Cys Phe Ala Tyr Ile Ala Arg Pro Leu Pro Arg Ala His Ile
            50                  55                  60

Lys Glu Tyr Phe Tyr Thr Ser Gly Lys Cys Ser Asn Pro Ala Val Val
65                  70                  75                  80

Phe Val Thr Arg Lys Asn Arg Gln Val Cys Ala Asn Pro Glu Lys Lys
                    85                  90                  95

Trp Val Arg Glu Tyr Ile Asn Ser Leu Glu Met Ser
                100                 105
```

<210> SEQ ID NO 7
<211> LENGTH: 348
<212> TYPE: DNA
<213> ORGANISM: Artificial Sequence
<220> FEATURE:

```
<223> OTHER INFORMATION: RANTES + IgE+ Kozak + RR SITES nucleic acid
      sequence

<400> SEQUENCE: 7
gaattcgcca ccatggactg gacctggatc ctgttcctgg tggccgctgc cacaagagtg       60
cacagcaagg tgtccgccgc cgccctggcc gtgatcctga tcgccaccgc cctgtgtgcc      120
cctgccagcg ccagccccta cagcagcgac accacccct gctgcttcgc ctacatcgcc       180 agaccctgc ccagagccca tcaaggag tacttctaca ccagcggcaa gtgtagcaat         240
cccgccgtgg tgttcgtgac ccggaagaac agacaagtgt gcgccaaccc cgagaagaag      300
tgggtgaggg agtacatcaa cagcctggag atgagctgat gactcgag                   348

<210> SEQ ID NO 8
<211> LENGTH: 108
<212> TYPE: PRT
<213> ORGANISM: Artificial Sequence
<220> FEATURE:
<223> OTHER INFORMATION: RANTES + IgE+ Kozak + RR SITES amino acid
      sequence

<400> SEQUENCE: 8

Met Asp Trp Thr Trp Ile Leu Phe Leu Val Ala Ala Thr Arg Val
1               5                   10                  15

His Ser Lys Val Ser Ala Ala Ala Leu Ala Val Ile Leu Ile Ala Thr
            20                  25                  30

Ala Leu Cys Ala Pro Ala Ser Ala Ser Pro Tyr Ser Ser Asp Thr Thr
        35                  40                  45

Pro Cys Cys Phe Ala Tyr Ile Ala Arg Pro Leu Pro Arg Ala His Ile
    50                  55                  60

Lys Glu Tyr Phe Tyr Thr Ser Gly Lys Cys Ser Asn Pro Ala Val Val
65                  70                  75                  80

Phe Val Thr Arg Lys Asn Arg Gln Val Cys Ala Asn Pro Glu Lys Lys
                85                  90                  95

Trp Val Arg Glu Tyr Ile Asn Ser Leu Glu Met Ser
                100                 105
```